(12) United States Patent
Rastogi et al.

(10) Patent No.: US 10,792,508 B2
(45) Date of Patent: Oct. 6, 2020

(54) QUADRUPLE BUTTERFLY COIL

(71) Applicants: Priyam Rastogi, Ames, IA (US); Erik Gordon Lee, Cambridge, MA (US); Magundappa Ravi L. Hadimani, Glen Allen, VA (US); David C. Jiles, Ames, IA (US)

(72) Inventors: Priyam Rastogi, Ames, IA (US); Erik Gordon Lee, Cambridge, MA (US); Magundappa Ravi L. Hadimani, Glen Allen, VA (US); David C. Jiles, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 268 days.

(21) Appl. No.: 15/795,057

(22) Filed: Oct. 26, 2017

(65) Prior Publication Data

US 2018/0117352 A1    May 3, 2018

Related U.S. Application Data

(60) Provisional application No. 62/416,603, filed on Nov. 2, 2016.

(51) Int. Cl.
*A61N 2/02* (2006.01)
*G01R 33/421* (2006.01)
(Continued)

(52) U.S. Cl.
CPC ............ *A61N 2/02* (2013.01); *A61B 5/04008* (2013.01); *G01R 33/4215* (2013.01);
(Continued)

(58) Field of Classification Search
CPC .................................................. A61N 2/00–12
See application file for complete search history.

(56) References Cited

U.S. PATENT DOCUMENTS

2010/0185042 A1    7/2010  Schneider et al.
2010/0286470 A1 * 11/2010  Schneider .............. A61N 2/006
                                                                            600/14
(Continued)

FOREIGN PATENT DOCUMENTS

WO    WO-2016116747 A1 *  7/2016 ............ A61N 2/006

OTHER PUBLICATIONS

U.S. Appl. No. 15/335,286, Jiles et al., filed Oct. 26, 2016.
(Continued)

*Primary Examiner* — Thaddeus B Cox
(74) *Attorney, Agent, or Firm* — Reinhart Boerner Van Deuren P.C.

(57) ABSTRACT

Provided herein are embodiments of a Quadruple Butterfly Coil (QBC) configuration having enhanced focality for stimulation of specific areas of a brain for therapeutic treatment. Finite element simulations were conducted for the QBC, the QBC with a single shield, and the QBC with a double shield. The stimulation profiles for these coil configurations were assessed with 50 anatomically realistic MRI derived head models. The coils were positioned on the vertex and the scalp over the dorsolateral prefrontal cortex to stimulate the brain. Computer modeling of the coils was performed to determine volume of stimulation, maximum electric field, location of maximum electric field, and area of stimulation across all 50 head models for both coils.

20 Claims, 15 Drawing Sheets
(7 of 15 Drawing Sheet(s) Filed in Color)

(51) Int. Cl.

| | |
|---|---|
| *A61B 5/04* | (2006.01) |
| *A61B 5/055* | (2006.01) |
| *A61N 1/36* | (2006.01) |
| *G01R 33/34* | (2006.01) |
| *A61B 5/0476* | (2006.01) |
| *A61N 1/04* | (2006.01) |
| *A61N 2/00* | (2006.01) |

(52) U.S. Cl.
CPC ............ *A61B 5/0476* (2013.01); *A61B 5/055* (2013.01); *A61N 1/0456* (2013.01); *A61N 1/36025* (2013.01); *A61N 2/006* (2013.01); *G01R 33/34046* (2013.01)

(56) References Cited

U.S. PATENT DOCUMENTS

| | | | |
|---|---|---|---|
| 2010/0331602 A1* | 12/2010 | Mishelevich | A61N 2/006 600/13 |
| 2015/0099921 A1 | 4/2015 | Schneider | |
| 2017/0120065 A1 | 5/2017 | Jiles et al. | |
| 2018/0369601 A1* | 12/2018 | Saitoh | A61F 2/04 |

OTHER PUBLICATIONS

A. Rotem et al., "Solving the orientation specific constraints in transcranial magnetic stimulation by rotating fields"; *PLoS One*, vol. 9, No. 2, 2014.

L. J. Crowther et al., "Transcranial magnetic stimulation: Improved coil design for deep brain investigation"; *J Appl. Phys.*, vol. 109, No. 7, p. 07B314, 2011.

L. Crowther et al., "Improved transcranial magnetic stimulation coil design with realistic head modeling", *Bull. Am. Phys. Soc.*, vol. vol. 58, No. 1, Mar. 2013.

Y. Meng et al., "Deep brain transcranial magnetic stimulation using variable 'Halo coil' system"; *J Appl. Phys.*, vol. 117, No. 17, p. 17B305, May 2015.

S. March et al., "Novel transcranial magnetic stimulation coil for mice"; *Bull. Am. Phys. Soc.*, vol. 59, 2014.

Z. D. Deng et al., "Electric field depth-focality tradeoff in transcranial magnetic stimulation: simulation com arison of 50 coil designs"; *Brain Stimul.*, vol. 6, No. 1, pp. 1-13, Jan. 2013.

Stephen D. March et al., "Thermal and Mechanical Analysis of Novel Transcranial Magnetic Stimulation Coil for Mice"; IEEE Transaction on Magnetics; vol. 50, No. 9; Sep. 2014.

S.D. March et al., "Focused and Deep Brain Magnetic Stimulation Using New Coil Design in Mice"; 6th Annual International IEEE EMBS Conference on Neural Engineering, San Diego, California, Nov. 6-8, 2013; pp. 125-128.

S. Ueno et al.; Localized stimulation of neural tissues in the brain by means of a paired configuration of time-varying magnetic fields; 4 pages; Journal of Applied Physics 64, 5862; 1988.

S. Ueno et al.; Functional mapping of the human motor cortex obtained by focal and vectorial magnetic stimulation of the brain; IEEE Transactions on Magnetics, 6 pages, vol. 26, No. 5, Sep. 1990.

\* cited by examiner

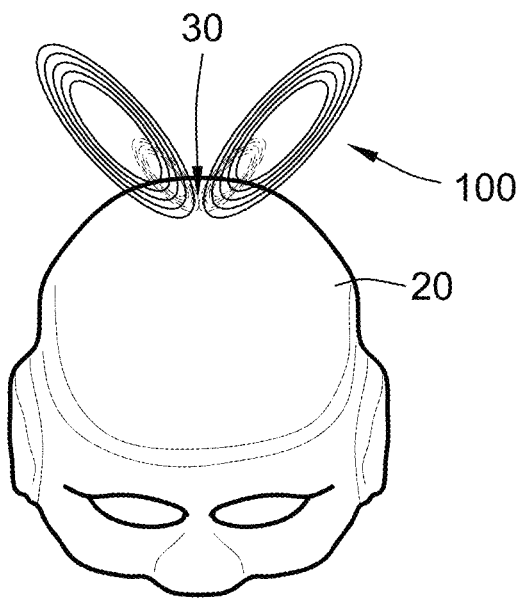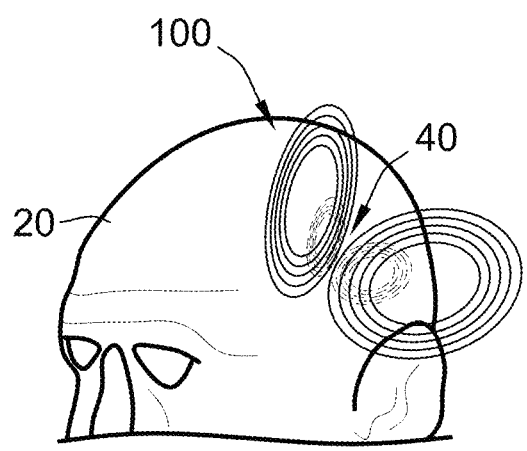
FIG. 2A  FIG. 2B
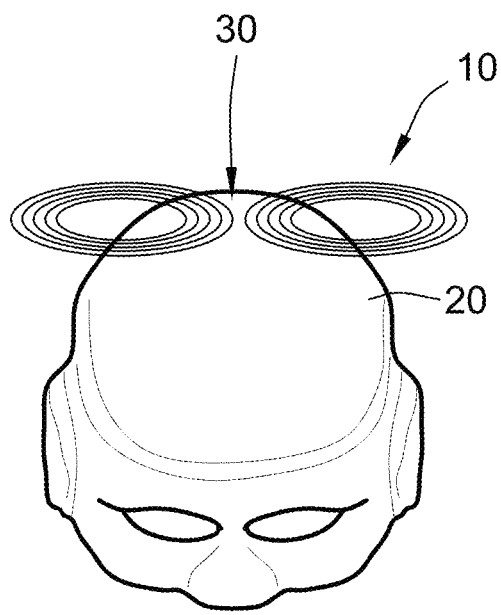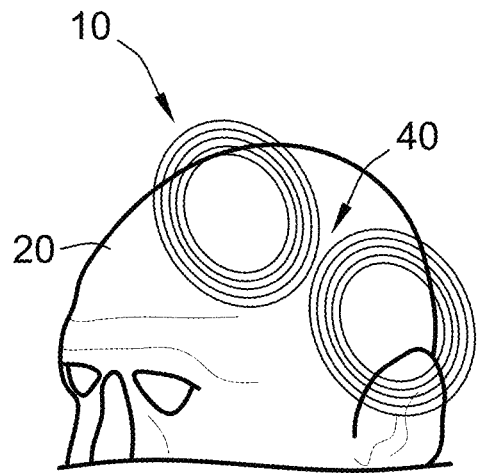
FIG. 3A  FIG. 3B

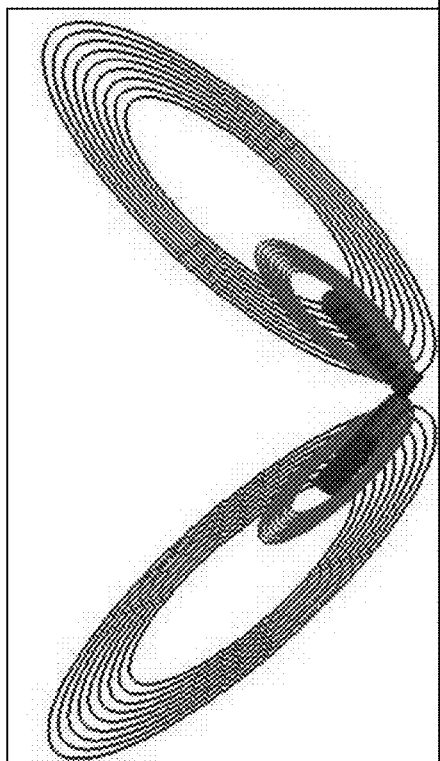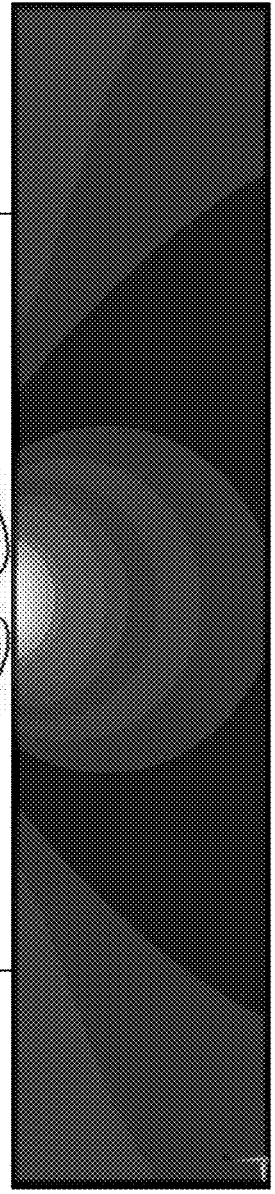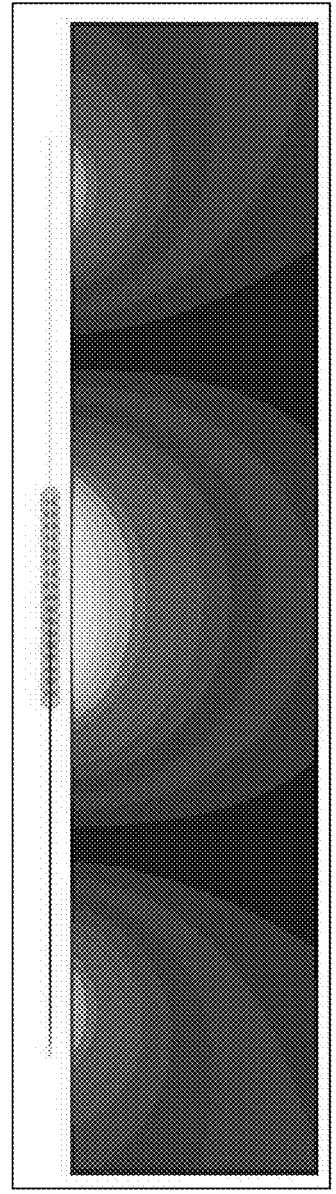
FIG. 4E
FIG. 5E

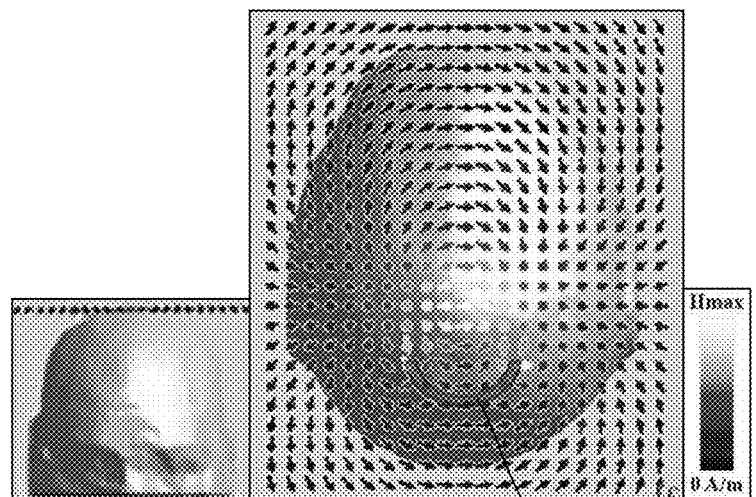
FIG. 24 — 210
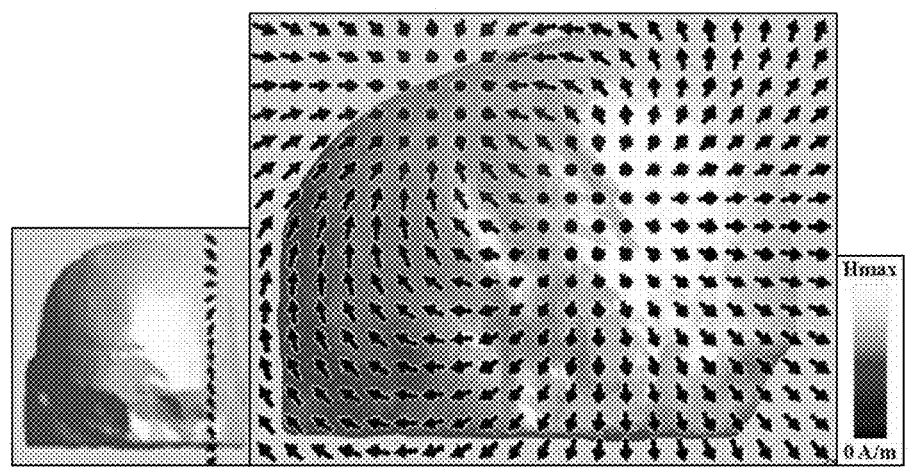
FIG. 25
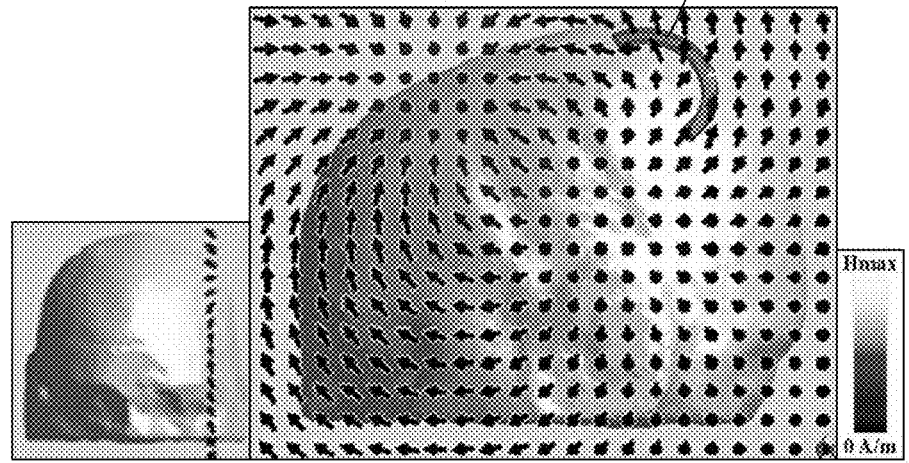
FIG. 26

QUADRUPLE BUTTERFLY COIL

CROSS-REFERENCE TO RELATED PATENT APPLICATION

This patent application claims the benefit of U.S. Provisional Patent Application No. 62/416,603, filed Nov. 2, 2016, the entire teachings and disclosures of these applications are incorporated herein by reference thereto.

FIELD OF THE INVENTION

This invention generally relates to an electromagnetic coil device for stimulation of biological tissues, especially brain tissue stimulation. More particularly, embodiments of the device have potential use as a therapeutic or neuroscience research device that uses electromagnetic coils to stimulate the brain for treatment and/or diagnosis of neurological disorders and for general research.

BACKGROUND OF THE INVENTION

Transcranial Magnetic Stimulation (TMS) is a technique for neuromodulation that can be used as a non-invasive therapy for various psychiatric and neurological disorders. In TMS, a time varying magnetic field generated from an electromagnetic coil placed on the scalp is used to induce an electric field inside the brain.

TMS has therapeutic effect for neurological disorders such as major depressive disorder, stroke, obsessive compulsive disorder, traumatic brain injury, Parkinson's disease, and post-traumatic stress disorder. The time varying magnetic field generated from a TMS coil will induce an electric field and cause depolarization of neurons. TMS can be administered as a single pulse or a train of pluses, which is called repetitive TMS (rTMS). Different repetition rates, also called stimulation frequencies, can be used to either up regulate or down regulate neuronal activity. The ability to modulate the activity of neural networks noninvasively and relatively painlessly allows researchers to explore brain stimulation as a tool to treat disease with much more ease than previous neuromodulation techniques such as deep brain stimulation (DBS) and electroconvulsive therapy (ECT) have allowed.

TMS coil geometry plays an important role in determining the focality and depth of penetration of the induced electric field responsible for stimulation. For instance, a "Triple Halo Coil" design has been proposed in U.S. application Ser. No. 15/335,286, filed on Oct. 26, 2016, and owned by a common assignee to the present application, which provides stimulation of deep regions of the brain. U.S. application Ser. No. 15/335,286 is incorporated in its entirety herein by reference. Additionally, many coils designed in the last twenty years have utilized different geometrical layouts, but no coils have shown significant improvement in focality over the Figure-8 coils while maintaining the field intensity required to stimulate at the depth of the surface of the brain. The Figure-8 coil configuration was first proposed by Ueno et al. in 1988 (see S. Ueno, T. Tashiro, and K. Harada, J. Appl. Phys. 64, 5862 (1988)) and functional mapping of the motor cortex was successfully obtained in a 5 mm resolution in 1990 by the same group (see S. Ueno, T. Matsuda, and M. Fujiki, IEEE Trans. Magn. 26, 1539 (1990)). Both Ueno references are incorporated in their entireties herein by reference.

Any development of TMS coils that allow for stimulation beyond the resolution of Figure-8 coils will give researchers more opportunities to stimulate specific neural circuits that are identified to be important in neurological disorders. This also avoids the modulation of neighboring brain regions whose relationship with a given disease may be unknown or dissimilar to that of the target stimulation site.

In addition to increased stimulation focality in the brain, coils that are able to reduce the spread of stimulation on the scalp may allow for stimulation of brain regions that are currently unreachable because of the practical consideration that widespread scalp stimulation generates uncomfortable muscle contractions over certain areas of the head. This is especially relevant for stimulation areas near the forehead aimed at the orbitofrontal cortex or near the back of the head aimed at the cerebellum.

Beyond therapeutics, as researchers further use TMS to explore different physiological measures or concurrent TMS & fMRI (Functional magnetic resonance imaging), TMS & EEG (electroencephalogram), or TMS & PET (positron emission tomography), more focal stimulation will be desired as it allows for more direct understanding of TMS outcomes.

The invention provides such a new magnetic coil configuration that enhances the focality of the electrical fields induced on the brain and over the scalp. These and other advantages of the invention, as well as additional inventive features, will be apparent from the description of the invention provided herein.

BRIEF SUMMARY OF THE INVENTION

In an embodiment, a novel Quadruple Butterfly Coil (QBC) configuration is disclosed that has an improved focality over the conventional Magstim 70 mm Figure-8 Coil (hereinafter referred to as "Figure-8 coil").

Finite element simulations were conducted with both the QBC and the conventional Figure-8 coil to compare coil characteristics. The stimulation profiles for the two coils were assessed with 50 anatomically realistic MRI derived head models. The coils were positioned on the vertex and the scalp over the dorsolateral prefrontal cortex to stimulate the brain. Computer modeling of the coils was performed to determine volume of stimulation, maximum electric field, location of maximum electric field, and cortical surface area of stimulation across all 50 head models for both coils.

In one aspect, embodiments of a stimulation device are provided. The stimulation device includes a first set of electromagnetic coils, including a first coil and a second coil, and a second set of electromagnetic coils, including a third coil and a fourth coil. An angle between the first coil and the second coil is less than 180°, and an angle between the third coil and the fourth coil is less than 180°. Additionally, the third coil is smaller in at least one dimension than the first coil, and the fourth coil is smaller in at least one dimension that the second coil.

In an embodiment of the stimulation device, the first coil and the second coil are the same size and shape, and the third coil and the fourth coil are the same size and shape. In a further embodiment, the third coil is at least 50% smaller in the at least one dimension than the first coil, and the fourth coil is at least 50% smaller in the at least one dimension than the second coil. In such an embodiment, the coils are all circular and the smaller coils are smaller in the dimension of their outside diameter.

In another embodiment of the stimulation device, the angle between the first coil and the second coil and the angle between the third coil and the fourth coil are each less than 150°. In a more specific embodiment, the angle between the first coil and the second coil and the angle between the third coil and the fourth coil are each 45°.

In an embodiment of the stimulation device, the current supplied to the coils is from 1 A to 10 kA and, in particular, at a frequency of 1 kHz to 10 kHz. In a more specific embodiment, the current supplied to the coils is from 2 kA to 5 kA at a frequency of 2.5 kHz. In another specific embodiment, the stimulation device is used to induce an electric field in grey matter near the threshold for neuronal depolarization, or in the range of 150 V/m (e.g., in the range of from 125 V/m to 175 V/m).

In another aspect, the stimulation device includes passive shielding to further enhance the focality. In an embodiment, each passive shield is made of a ferromagnetic material. Further, in embodiments, each passive shield is a semi-circular bar with an inside diameter from 40 mm to 55 mm and an outside diameter from 50 mm to 70 mm. In still further embodiments, each shield has a thickness of from 2 mm to 5 mm.

In still another aspect, embodiments of a stimulation method are provided. The method involves positioning a stimulation device as described above over a head. Current is supplied to the stimulation device, and neural networks of the brain are stimulated.

In an embodiment of the method, the stimulation device is positioned over the vertex of the head. Further, in embodiments, a first ferromagnetic shield is positioned a lateral distance of from 20 mm to 30 mm away from the stimulation device and towards the rear of the head. In a further embodiment, a second ferromagnetic shield is positioned a lateral distance of from 50 mm to 60 mm away from the stimulation device and towards the front of the head.

In still another embodiment of the method, the stimulation device is positioned over the dorsolateral prefrontal cortex of the head. Further, in embodiments, a first ferromagnetic shield is positioned a lateral distance of from 80 mm to 90 mm away from the stimulation device and towards the rear of the head. In a further embodiment, a second ferromagnetic shield is positioned a lateral distance of from 70 mm to 90 mm away from the stimulation device and towards the front of the head.

Other aspects, objectives and advantages of the invention will become more apparent from the following detailed description when taken in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings incorporated in and forming a part of the specification illustrate several aspects of the present invention and, together with the description, serve to explain the principles of the invention.

FIGS. 2A-2B depict the QBC on the vertex position of a human head model (FIG. 2A) and on the dorsolateral prefrontal cortex position (FIG. 2B), according to an exemplary embodiment.

FIGS. 3A-3B depict the Figure-8 coil located at the vertex position of a human head model (FIG. 3A) and on the dorsolateral prefrontal cortex position (FIG. 3B), according to an exemplary embodiment.

FIG. 4E depicts the induced electric field in relation to the QBC, according to an exemplary embodiment on a simplified model.

FIG. 5E depicts the induced electric field in relation to the Figure-8 coil, according to an exemplary embodiment on a simplified model.

FIG. 24 depicts the magnetic vector field produced by the QBC with single shield located at the vertex position.

FIG. 25 depicts the magnetic vector field produced by the QBC located at the dorsolateral prefrontal cortex position.

FIG. 26 depicts the magnetic vector field produced by the QBC with single shield located at the dorsolateral prefrontal cortex position.

Figure 1:
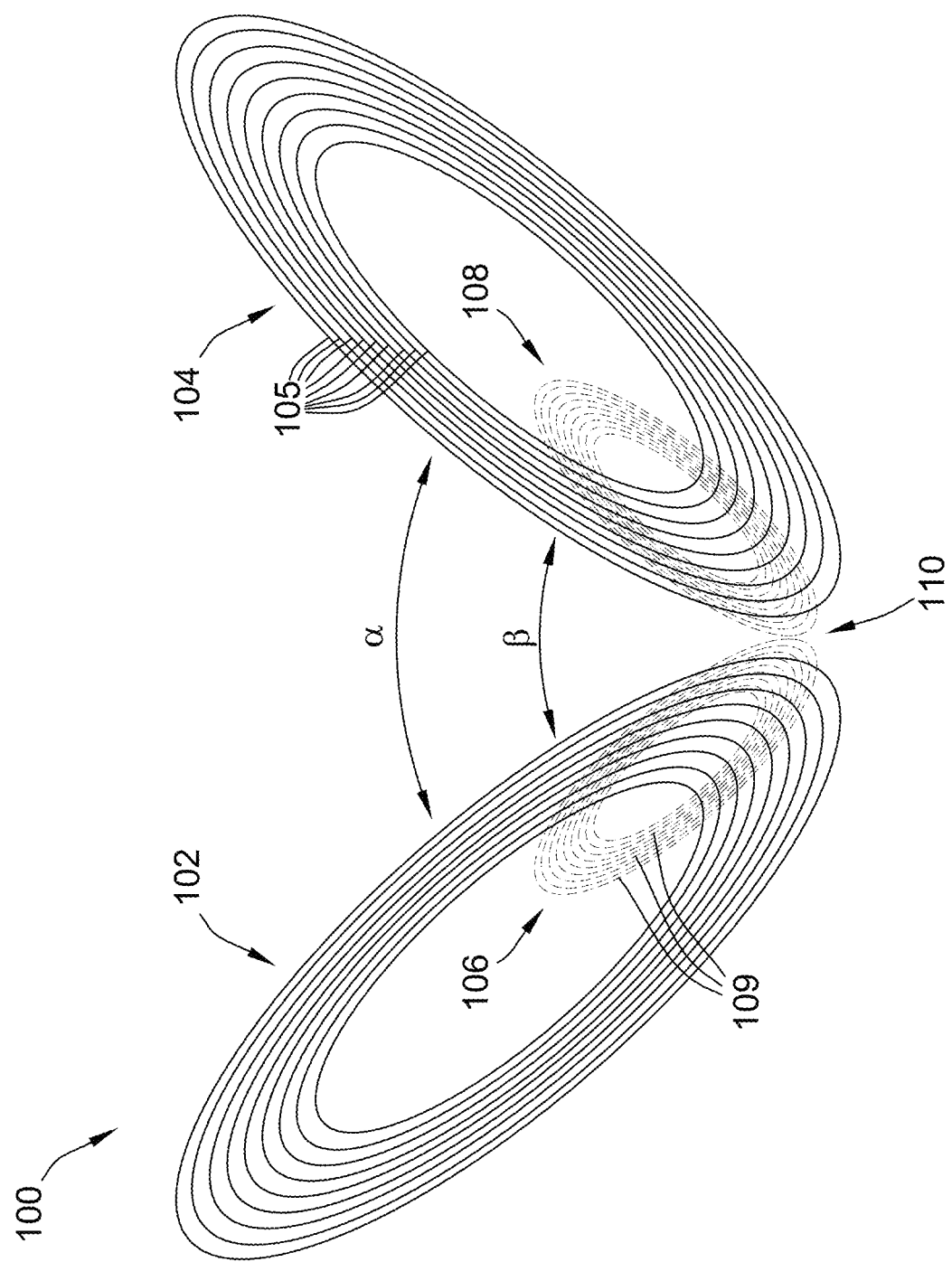
FIG. 1 is a depiction of a Quadruple Butterfly Coil (QBC) according to an embodiment of the present invention.
Figure 4B:
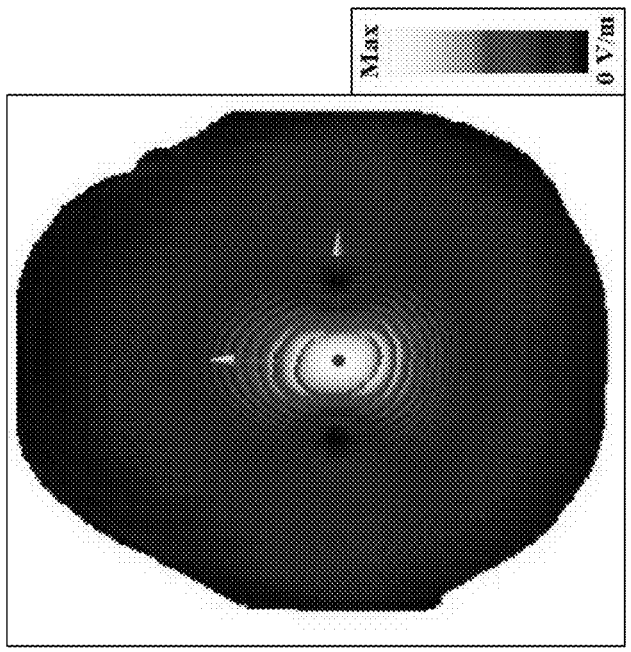
FIGS. 4A-4D depict the induced electric field produced by the QBC on the grey matter (FIG. 4A) and scalp (FIG. 4B) in the vertex position and on the grey matter (FIG. 4C) and scalp (FIG. 4D) in the dorsolateral prefrontal cortex position.
Figure 4D:
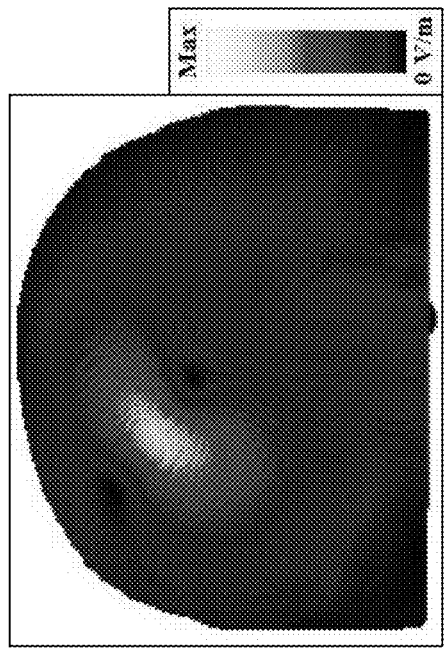
Figure 4A:
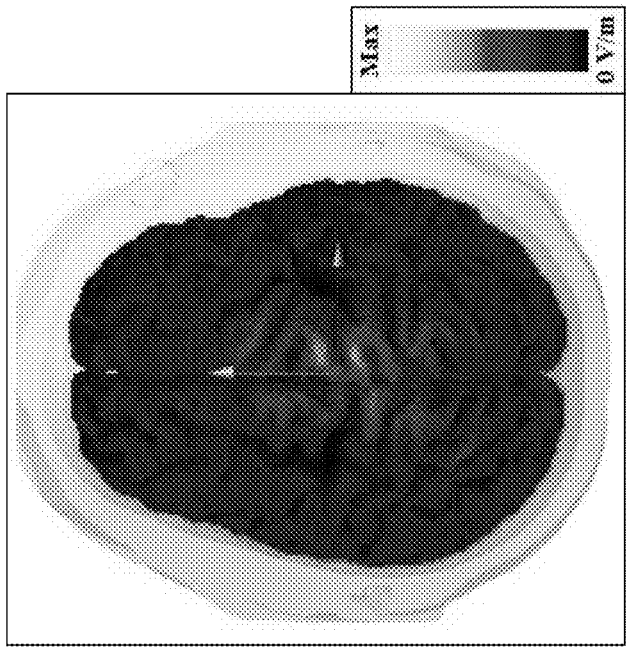
Figure 4C:
Figure 5B:
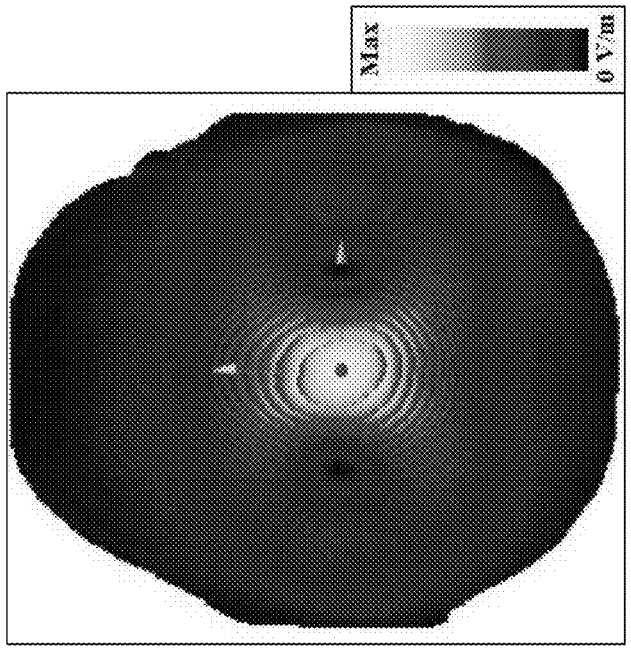
FIGS. 5A-5D depict the induced electric field produced by the Figure-8 on the grey matter (FIG. 5A) and scalp (FIG. 5B) in the vertex position and on the grey matter (FIG. 5C) and scalp (FIG. 5D) in the dorsolateral prefrontal cortex position.
Figure 5D:
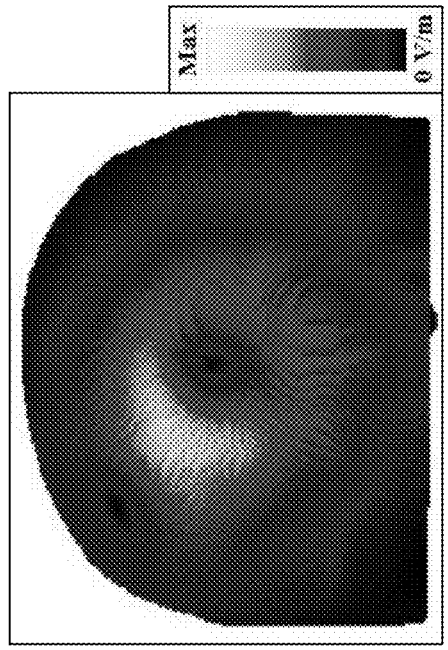
Figure 5A:
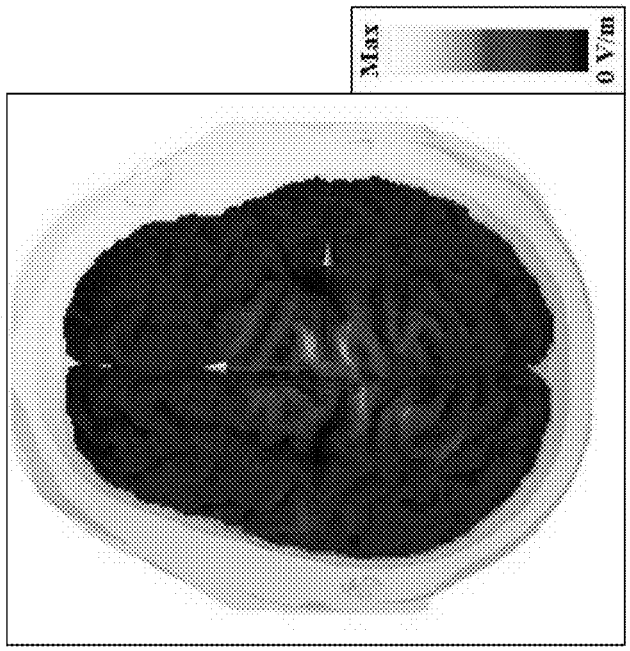
Figure 5C:
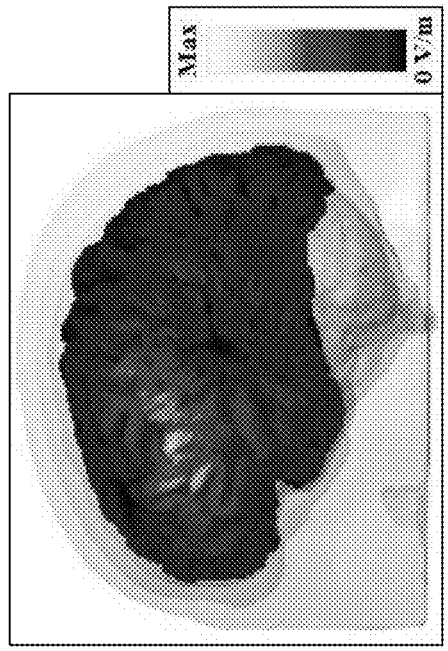

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Embodiments of a stimulation device that utilizes electromagnetic coils are disclosed herein. The stimulation device includes two sets of coils, including a first larger set of coils and a second smaller set of coils. Each of the sets of coils is upwardly angled away from a subject's head so as to increase the focality of the induced electric field in the region directly below vertex of the coils. In embodiments described herein, a ferromagnetic material is used to provide passive shielding to further improve the focality. The stimulation device is referred to herein as a Quadruple Butterfly Coil (QBC), and the electric field (E-field) produced by the QBC was studied and compared to the E-field produced by a conventional Figure-8 coil. The studies were performed using simulations on a set of fifty anatomically varied head models.

The fifty head models used in the study were derived from Human Connectome Project subjects' MRI images, which were developed by E. G. Lee, W. Duffy, R. L. Hadimani, M. Waris, W. Siddiqui, F. Islam, M. Rajamani, R. Nathan, and D. C. Jiles, IEEE Trans. Magn. 52, 1 (2016), incorporated herein in its entirety by reference, using the SimNIBS pipeline. These models consist of seven different segmented anatomies including skin, skull, cerebrospinal fluid, grey matter (GM), white matter (WM), cerebellum and ventricles. Also, these models were created from healthy young adults in the age range from twenty-two to thirty-five years, with an equal number of female and male head models.

Calculation of the electric field (E-field) and modeling of TMS coils was performed using SEMCAD X and Sim4Life, which is an updated version of SEMCAD X and which allows for simulations that include ferromagnetic materials. The current supplied to the TMS coils was 5000 A peak to peak at a frequency of 2.5 kHz. Generally, the current supplied to the coil for TMS will be between 2000 A and 5000 A based on an individualized stimulation threshold. In other embodiments, the current supplied to the TMS coil ranges from 1 A to 10 kA and at frequencies ranging from 1 kHz to 10 kHz. The corresponding relative permittivity and electrical conductivity values were taken from K. N. Hasgall P A, Di Gennaro F, Baumgartner C, Neufeld E, Gosselin M C, Payne D, Klingenböck A, Version 3, (2015), which is incorporated herein in its entirety by reference. A quasi-static, low frequency solver was used for the calculation of the induced electric field in the brain and magnetic fields generated from the coils. Results from SEMCAD X were exported to MATLAB for data processing and construction of plots. A Magstim 70 mm double coil (Figure-8 coil), available from Magstim, Inc., Whitland, Wales, UK, was used as a comparison coil for the results with QBC. Results from the Figure-8 coil were included for the purposes of comparison, since this coil has been widely used and provided a reference for the results of the new QBC.

Referring to FIG. 1, the QBC 100 is designed with at least two sets of coils in which a first set of coils includes a first larger coil 102 and a second larger coil 104. The first larger coil 102 and the second larger coil 104 both contain a number of individual windings 105. In an embodiment, the first larger coil 102 and the second larger coil 104 contain between two and twenty windings 105. In another embodiment, the first larger coil 102 and the second larger coil 104 contain between five and fifteen windings 105. Further, the first larger coil 102 and the second larger coil 104 need not contain the same number of windings 105, and thus, in some embodiments, the first larger coil 102 and the second larger coil 104 contain a different number of windings 105. In the embodiment depicted, the first larger coil 102 and the second larger coil 104 both contain nine windings 105.

In embodiments, the two larger coils 102, 104 are as the same size. By "same size," it is meant that the two larger coils 102, 104 have the same dimensions. In the embodiment depicted, the two larger coils 102, 104 are circular, having an inner diameter at the innermost winding 105 and an outer diameter at the outermost winding 105. Thus, in embodiments, two larger coils 102, 104 that are the same size have the same inner diameter and the same outer diameter. However, in other embodiments, the two larger coils 102, 104 are differently sized. In that respect, the two larger coils 102, 104 are differently sized in at least one dimension. In still other embodiments, the two larger coils 102, 104 are differently shaped. As mentioned above, the depicted embodiment includes circular larger coils 102, 104. However, in other embodiments, the two larger coils 102, 104 take other curved or polygonal shapes, such as ovals, ellipses, racetracks, quadrilaterals, triangles, pentagons, hexagons, octagons, etc.

A second set of coils includes a first smaller coil 106 and a second smaller coil 108. As with the larger coils 102, 104, the smaller coils 106, 108 contain a number of individual windings 109. In an embodiment, the first smaller coil 106 and the second smaller coil 108 contain between two and twenty windings 109. In another embodiment, the first smaller coil 106 and the second smaller coil 108 contain between five and fifteen windings 109. Further, the first smaller coil 106 and the second smaller coil 108 need not contain the same number of windings 109, and thus, in some embodiments, the first smaller coil 106 and the second smaller coil 108 contain a different number of windings 109. In the embodiment depicted, the first smaller coil 106 and the second smaller coil 108 both contain nine windings 109.

In embodiments, the two smaller coils 106, 108 are as the same size. By "same size," it is meant that the two smaller coils 106, 108 have the same dimensions. In the embodiment depicted, the two smaller coils 106, 108 are circular, having an inner diameter at the innermost winding 109 and an outer diameter at the outermost winding 109. Thus, in embodiments, two smaller coils 106, 108 that are the same size have the same inner diameter and the same outer diameter. However, in other embodiments, the two smaller coils 106, 108 are differently sized. In that respect, the two smaller coils 106, 108 are differently sized in at least one dimension. In still other embodiments, the two smaller coils 106, 108 are differently shaped. As mentioned above, the depicted embodiment includes circular smaller coils 106, 108. However, in other embodiments, the two smaller coils 106, 108 take other curved or polygonal shapes, such as ovals, ellipses, racetracks, quadrilaterals, triangles, pentagons, hexagons, octagons, etc.

In an embodiment, the smaller coils 106, 108 are at most 50% of the size of the larger coils 102, 104, e.g., the outer diameter of the smaller coils 106, 108 is at most half the size of the outer diameter of the larger coils 102, 104. In an embodiment, the smaller coils 106, 108 are 40% of the size of the larger coils 102, 104, e.g., the outer diameter of the smaller coils 106, 108 is 0.4 times the size of the outer diameter of the larger coils 102, 104.

The first larger coil 102 forms an angle $\alpha$ with the second larger coil 104 with a vertex 110. The first smaller coil 106 forms an angle $\beta$ with the second smaller coil 108 in which vertex 110 is common to angles $\alpha$, $\beta$. In embodiments, the larger coils 102, 104 have an angle $\alpha$ of less than 180°, and the smaller coils 106, 108 have an angle $\beta$ of less than 180°. In an embodiment, the angles $\alpha$, $\beta$ between each of the two larger coils 102, 104 and the two smaller coils 106, 108 are the same. In a specific embodiment, angles $\alpha$, $\beta$ are both 45°, i.e., the coils are inclined 67.5° from a planar arrangement. Additionally, the coils on the left 102, 106 (with respect to the orientation of the QBC 100 in FIG. 1) and the coils on the right 104, 108 have current flowing through the windings 105, 109 in the same direction at the vertex 110, allowing for summation of field intensities.

In a further embodiment, the QBC 100 includes a third set of coils (not shown) arranged in a manner similar to the first and second set of coils. In particular embodiments, the third set of coils is smaller in size than the first and second set of coils. As with the other sets of coils, the coils of the third set are at an angle that is less than 180°, and in a particular embodiment, the angle between the coils of the third set is less than or equal to the angles $\alpha$ and/or $\beta$.

The smaller coils 106, 108 are added on top of larger coils 102, 104 in the QBC to increase the magnetic vector potential over the target stimulation site, which is decreased when the coils are angled upwards. This in turn increases the induced electric field in the QBC to be more comparable to that of a Figure-8 Coil, while maintaining the increased focality from the angle adjustment. The second set of coils, i.e., smaller coils 106, 108, was chosen to be smaller than the angled, larger coils 102, 104 to allow the QBC to localize the increased magnetic vector potential from the second set of coils 106, 108 to be more weighted towards the coil's desired location of stimulation, i.e. directly below the vertex 110 of the coils.

FIGS. 2A and 2B depict the QBC 100 at various positions on a human head model 20. In FIG. 2A, the QBC 100 is located at the vertex position 30 of the head model 20. In FIG. 2B, the QBC 100 is located at the dorsolateral prefrontal cortex position 40. FIG. 3A depicts the Figure-8 coil 10 in the vertex position 30, and FIG. 3B depicts the Figure-8 coil 10 in the dorsolateral prefrontal cortex position 40. Simulations of the E-field were performed at these locations on the head model 20, and the results are depicted in FIGS. 4A-D for the QBC 100 and in FIGS. 5A-D for the Figure-8 coil 10.

In FIGS. 4A-D and 5A-D, the induced electric field on the surface of grey matter (GM) and scalp from both the QBC and Figure-8 coil on the vertex and on the dorsolateral prefrontal cortex is shown. As can be seen when comparing these figure sets, the QBC provides increased focality towards the direction of the outer coil windings. Further, in comparing FIGS. 4B and 4D with FIGS. 5B and 5D, the images of the E-Field profile on the scalp illustrate that the QBC stimulates a much more focused portion of the scalp than the Figure-8 coil. It is envisioned that the ability of the QBC to stimulate more focally on the scalp may prove to be advantageous in settings where muscles near the TMS stimulation site cause excessive twitching in subjects receiving TMS. Further, as shown in FIGS. 4E and 5E, the QBC provides a more focused and less deep E-field directly below the center (or vertex 110) of the coil, while the Figure-8 coil provides a more expansive and deeper E-field that also extends to the outer edges of the coil.

Figures 6A, 6B, 6C:
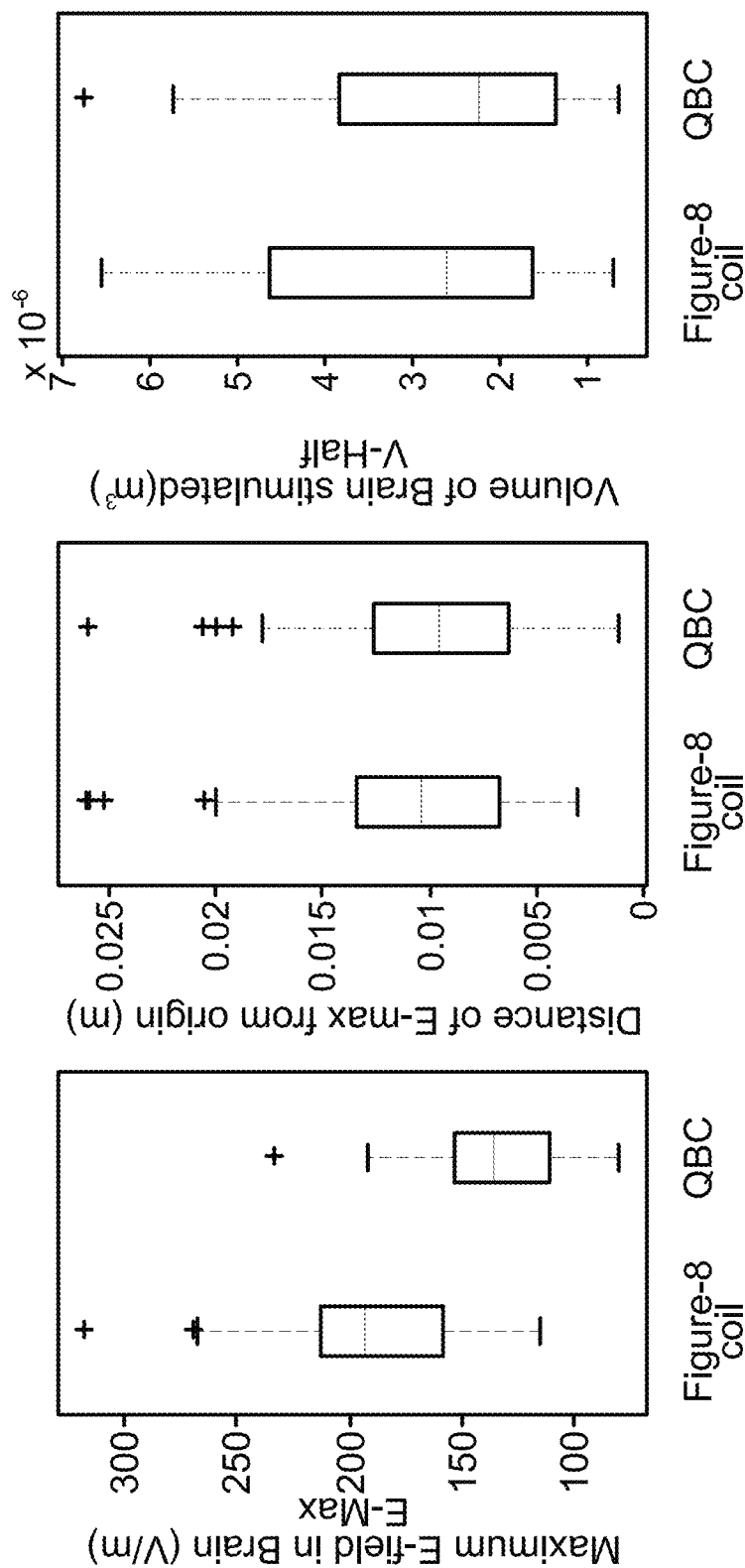
FIGS. 6A-6C depict sets of boxplots showing the five number summary (minimum, first quartile, median, third quartile and maximum, outliers) for E-max (Maximum E-field in Brain) (FIG. 6A), Distance of E-max from expected location (FIG. 6B), which is assumed to be directly beneath the center of the coil, and V-Half (Volume of Brain Stimulated with an E-field intensity greater than one half E-Max) (FIG. 6C) for Figure-8 coil and Quadruple Butterfly Coil using 50 set of head models, according to an exemplary embodiment.

The box plots in FIGS. 6A-6C illustrate three sets of data from the Figure-8 coil and the QBC collected from simulations of the coils placed over the vertex position of the head models. The first box plot in FIG. 6A shows the maximum electric field intensity in the brain (E-Max) for all 50 head models due to the Figure-8 coil and QBC. In particular, FIG. 6A provides the five number summary, including the minimum, first quartile, median, third quartile, and maximum, for E-max (V/m) for the Figure-8 coil and the QBC. The five number summary for the Figure-8 coil is 114.89 V/m, 158.16 V/m, 191.76 V/m, 213.1024 V/m, and 318.08 V/m, respectively. The five number summary for the QBC is 79.78 V/m, 111.17 V/m, 135.94 V/m, 153.12 V/m, and 233.88 V/m, respectively. Results show that the QBC stimulates at weaker intensities than the Figure-8 coil for a given current intensity, but both coils have a comparable ratio of electric field on scalp to brain (2.17 for QBC and 1.69 for Figure-8 at vertex), which is important for not over-stimulating nerves near the site of stimulation. The induced electric field intensity from both the coils are sufficient to meet standards which are required for neuronal depolarization as disclosed in M. Lu and S. Ueno, IEEE Trans. Magn. 9464, 1 (2015), which is incorporated herein in its entirety by reference.

The second box plot shown in FIG. 6B illustrates the location of E-Max relative to the expected E-Field maximum (i.e., directly below the vertex of the coil). This metric is relevant to understanding the precision of stimulation for the different coils. Results show there is an improvement of 8% in the QBC over the Figure-8 coil.

FIG. 6C depicts a third box plot showing the five number summary for a volume of brain stimulated with an electric field intensity greater than half of the max stimulation observed in the brain (referred to as "V-Half" and measured in units $m^3$). The five number summary for the Figure-8 coil is 6.91e-07 $m^3$, 1.63e-06 $m^3$, 3.02e-06 $m^3$, 4.65e-06 $m^3$, and 6.56e-06 $m^3$. For the QBC, the five number summary is 6.30e-07 $m^3$, 1.36e-06 $m^3$, 2.67e-06 $m^3$, 3.83e-06 $m^3$, and 6.74e-06 $m^3$. As shown in FIG. 6C, the QBC provides a decrease in the volume of the brain exposed to E-field intensities by 11.6% compared to Figure-8 coil, which is a significant reduction in stimulation of brain volume.

TABLE 1

Measure of interest for both QBC and Figure-8 coil on two positions.

| Measure of Interest (mean) | QBC | Figure-8 coil |
|---|---|---|
| Coil Positioned at Vertex | | |
| V-Half (m³) | 2.6709E−06 | 3.0E−06 |
| E-Max (GM&WM) (V/m) | 136 | 192 |
| Distance of E-Max from Origin (m) | 0.0102 | 0.0111 |
| A-Half (m²) | 0.0010 | 0.0011 |
| E-Max (Entire head) (V/m) | 296 | 325 |
| Coil Positioned at Dorsolateral Prefrontal Cortex | | |
| V-Half (m³) | 4.7568E−06 | 5.4481E−06 |
| E-Max (GM&WM) (V/m) | 156 | 230 |
| A-Half (m²) | 0.0018 | 0.0021 |
| E-Max (Entire head) (V/m) | 282 | 339 |

Table 1 gives the summary for both positions (vertex and dorsolateral prefrontal cortex) and coils and gives the means of E-max (on both GM & WM and on entire head), V-Half, distance of E-Max from expected location of maximum stimulation and area of stimulation. QBC has an advantage over the Figure-8 coil in terms of focality and can be used for TMS applications where focality is the main parameter of interest.

Figure 7A:
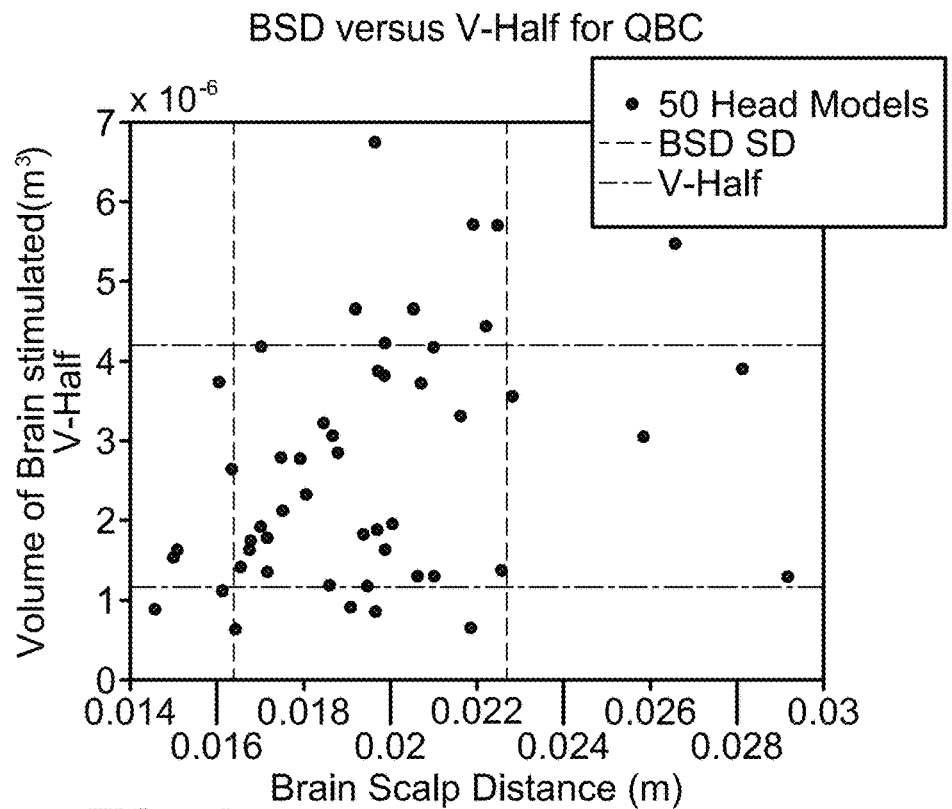
FIGS. 7A-7B depict scatter plots representing the relationship between a volume of brain stimulated with an electric field intensity greater than half of the max stimulation observed in the brain (V-Half) and brain scalp distance (BSD) for the QBC and for the position of the E-max along the sagittal and coronal plane, according to an exemplary embodiment.
Figure 7B:
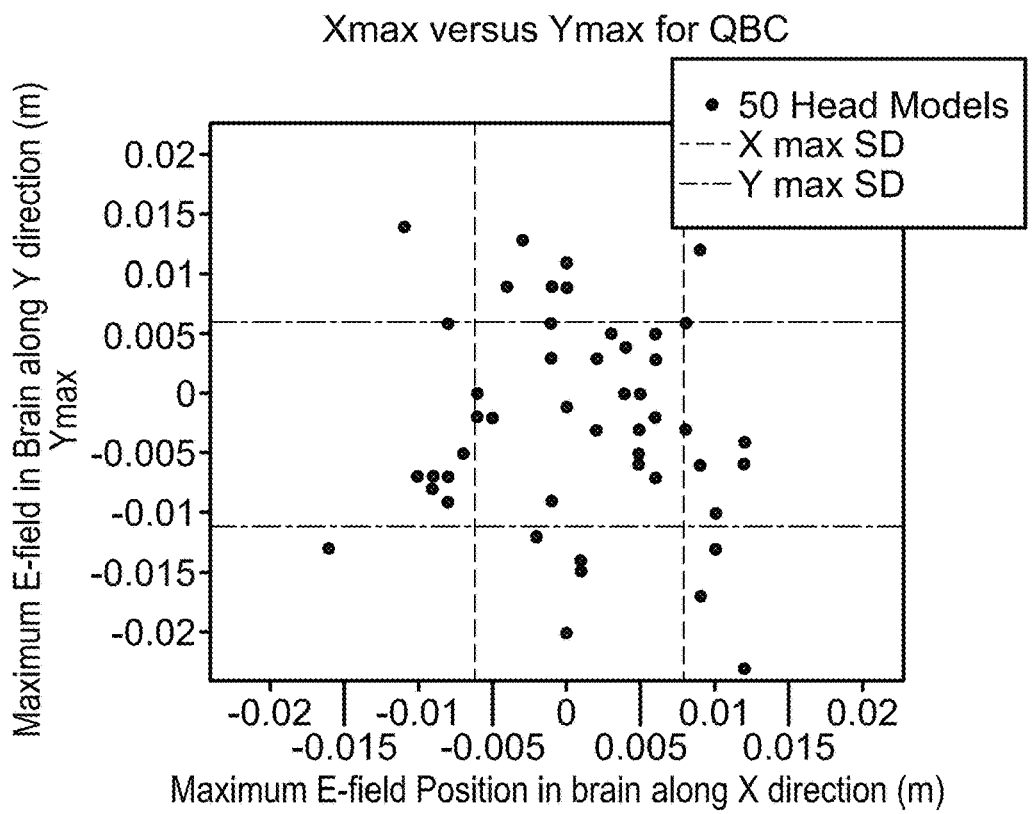
Figure 8A:
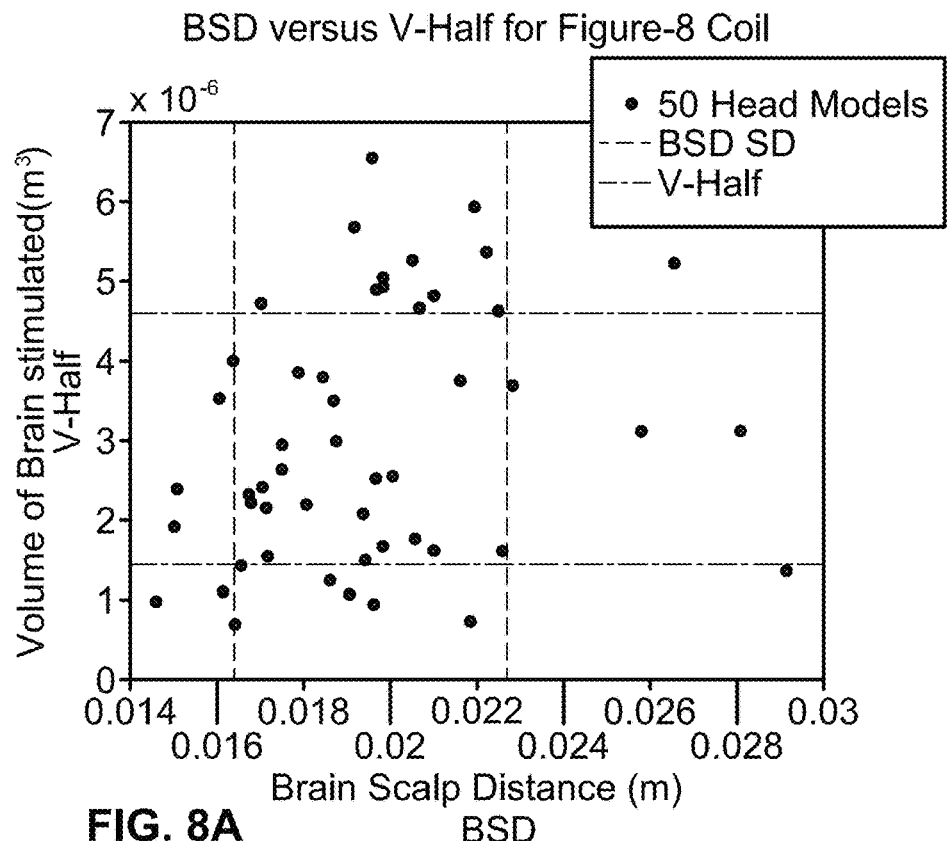
FIGS. 8A-8B depict scatter plots representing the relationship between V-Half and BSD for the Figure-8 and for the position of the E-max along the sagittal and coronal plane, according to an exemplary embodiment.
Figure 8B:
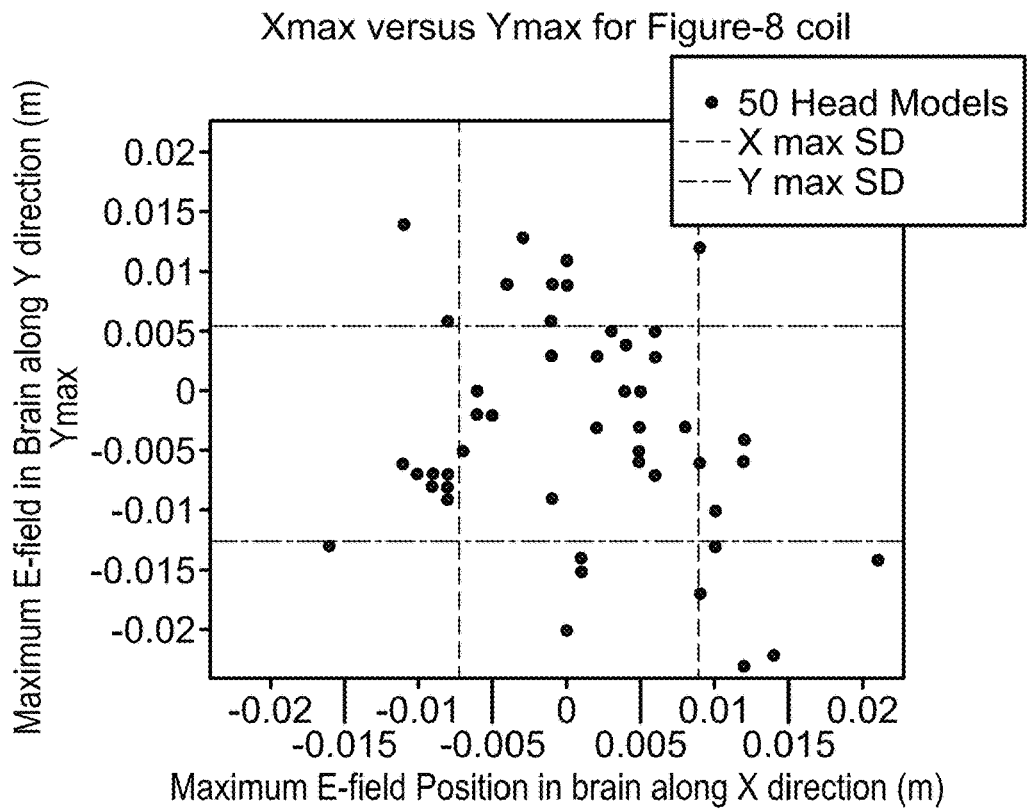

FIGS. 7A-7B depict scatter plots related to the QBC. FIG. 7A depicts the volume of brain stimulated with an electric field intensity greater than half of the max stimulation observed in the brain (V-Half) vs. brain scalp distance (BSD) with each plot point representing the measured V-Half and BSD values for each of the fifty head models. The dashed and dash-dot lines show the limits of standard deviations for the V-Half and BSD measurements. FIG. 7B shows a scatter plot for the location of the maximum E-field in the brain in the x and y direction as measured for each of the fifty head models. The dashed and dash-dot line depict the bounds of the standard deviations for the x and y measurements. FIGS. 8A and 8B depict the corresponding information for the Figure-8 coil. As can be seen when comparing FIGS. 7A-7B and FIGS. 8A-8B, more plot points from the fifty head models fall within the standard deviation of the measured properties for the QBC than for the Figure-8 coil.

Figure 9:
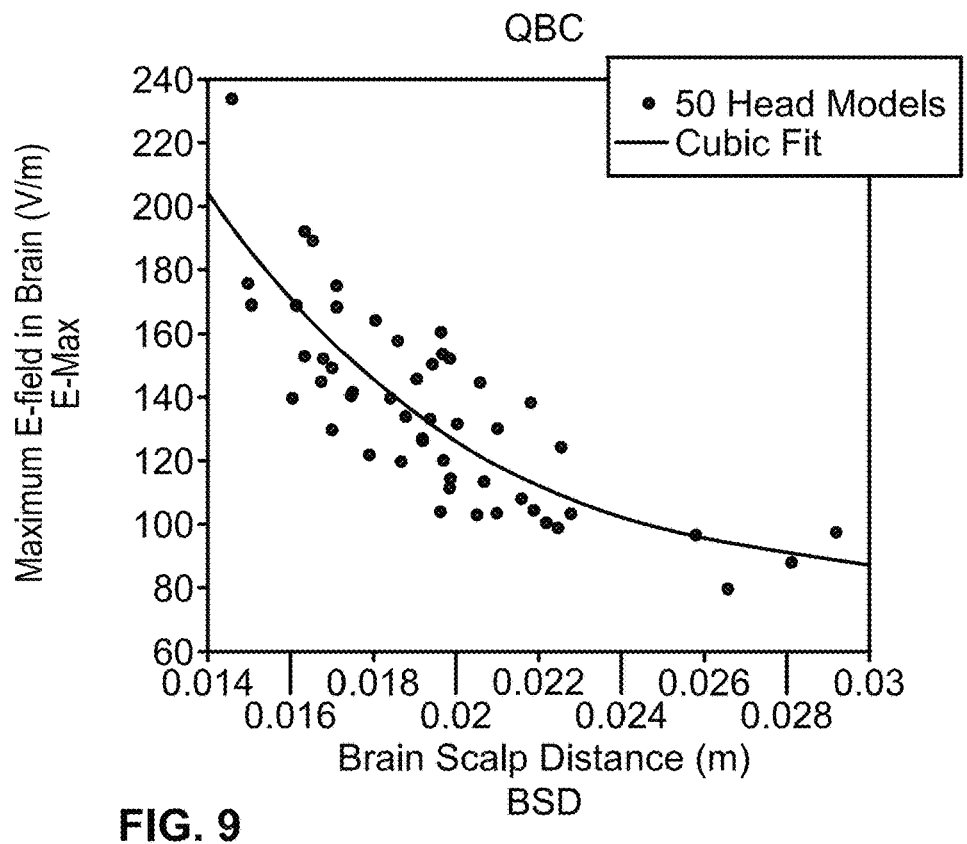
FIG. 9 depicts the maximum E-field and Brain Scalp Distance (BSD) for the QBC, according to an exemplary embodiment.
Figure 10:
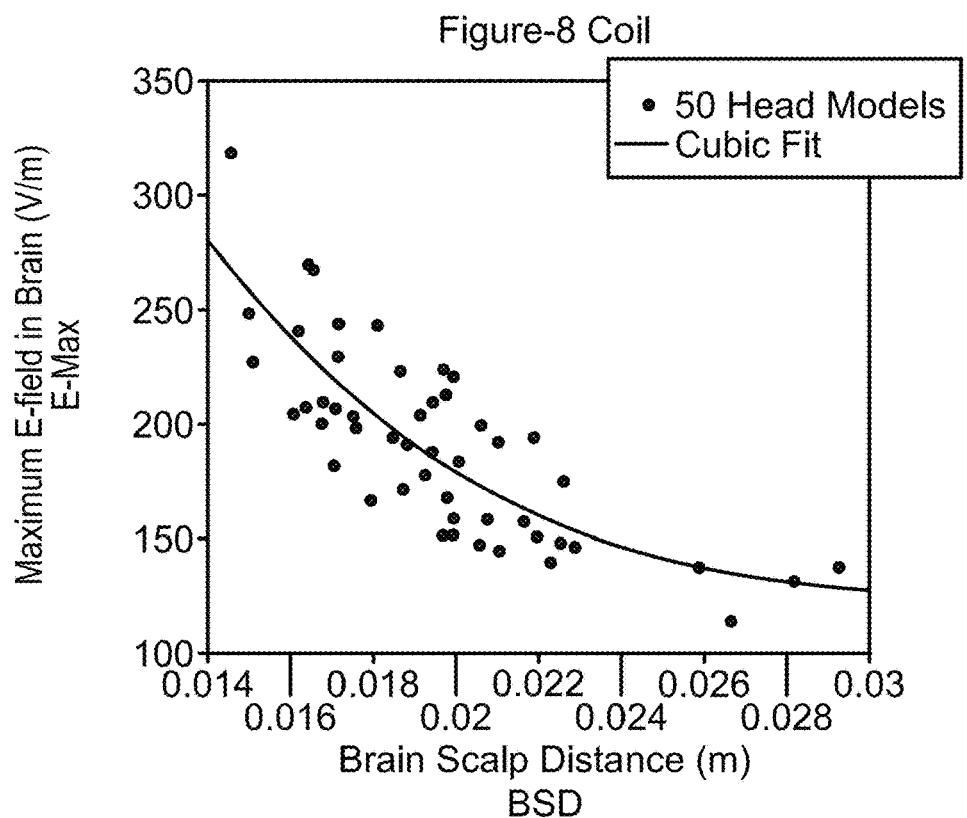
FIG. 10 depicts the maximum E-field and Brain Scalp Distance (BSD) for the Figure-8 coil, according to an exemplary embodiment.

FIGS. 9 and 10 depict the maximum E-field in the brain as compared to the brain scalp distance. As expected for both the QBC and the Figure-8, the maximum E-field decreased at an exponential rate with increasing BSD.

As disclosed herein, a novel coil design QBC is proposed, which improves focality as compared to the Magstim 70 mm Figure-8 coil. The QBC coil has been positioned at two different locations on the head and the TMS induced stimulation profile was calculated for 50 head models. Advantageously, the stimulation device is able to induce an electric field in grey matter near the threshold for neuronal depolarization, especially for depolarization of cortical neurons, which is about 150 V/m (e.g., in the range of from 125 V/m to 175 V/m).

In embodiments of the QBC, electromagnetic shielding can optionally be used to further improve the focality of the QBC in the direction perpendicular to the width of the QBC, i.e., in the forward and backward direction of the head as shown in FIG. 2A. For example, conductive shielding plates can be included to improve the focality of the induced electric field. In another example, active shields are utilized. The active shields consist of additional coils disposed above and/or around the QBC that carry current of the opposite polarity. The current magnitude, vertical position, and radius of the active shielding coils can be manipulated to provide the desired focality. In another exemplary embodiment, ferromagnetic cores are used to provide shielding of desired regions. By utilizing such exemplary shielding techniques, further improvement to the focality of the induced electric field can be provided.

Figure 11:
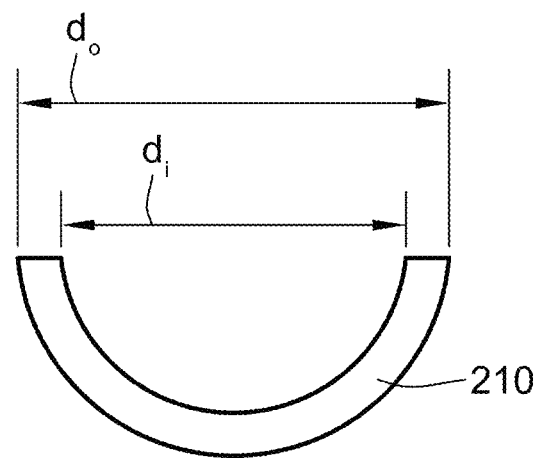
FIG. 11 depicts a top view of a passive shield for use with the QBC, according to an exemplary embodiment.
Figure 12:
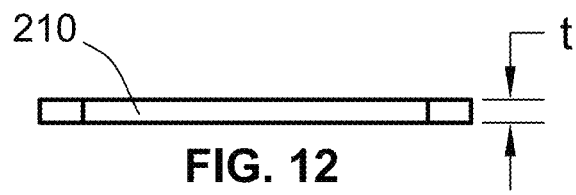
FIG. 12 depicts a side view of the passive shield of FIG. 11.

In another embodiment, a ferromagnetic material was used as a passive shield to further improve the focality of stimulation. In a particular embodiment, the ferromagnetic material used as a passive shield is Mu-metal. In embodiments, the passive shield is positioned in between a patient's head and the QBC. FIG. 11 provides an embodiment of the passive shield 210 that is in the shape of a semi-circle. In embodiments, the passive shield 210 has an inner diameter $d_i$ of from 40 mm to 55 mm. In the depicted embodiment, the inner diameter $d_i$ is 48 mm. Still further, in embodiments, the passive shield 210 has an outer diameter $d_o$ of from 50 mm to 70 mm. In the depicted embodiment, the outer diameter $d_o$ is 60 mm. Referring now to FIG. 12, in embodiments, the passive shield 210 has a thickness t of from 2 mm to 5 mm. In a particular embodiment, the thickness t is 3 mm. While the passive shield 210 depicted in FIGS. 11 and 12 is semi-circular in shape, other shapes can also be used for the passive shield 210, such as parabolic, V-shaped, rectangular, and brick-shaped, among others.

Figure 13:
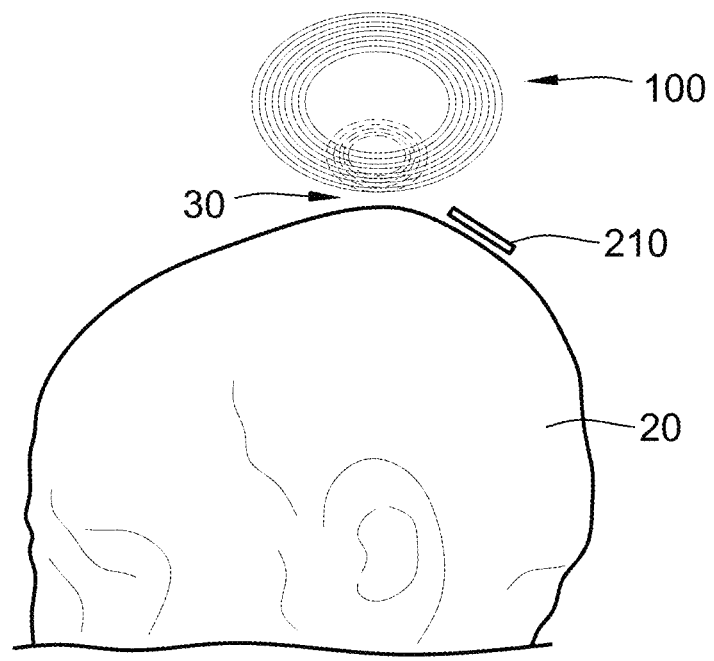
FIG. 13 depicts a QBC with single shield in the vertex position over a head model, according to an exemplary embodiment.
Figure 14:
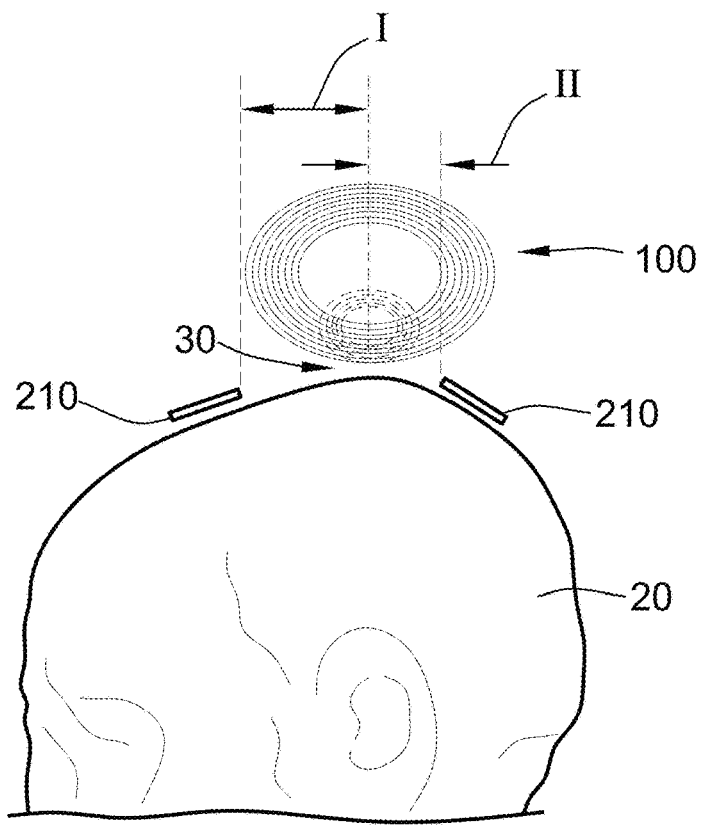
FIG. 14 depicts a QBC with double shield in the vertex position over a head model, according to an exemplary embodiment.

As can be seen in FIGS. 13 and 14, a space is provided between the patient's head (i.e., head model 20) and the passive shield 210 in the single shield embodiment and between the head model 20 and the passive shields 210 in the double shield embodiment. In an embodiment, the space is from 1 to 5 mm. In the depicted embodiment, the space is approximately 2.5 mm. Further, in the depicted embodiment, a space is provided between the head model 20 and the QBC 100. In a particular embodiment, the space between the head model 20 and the QBC 100 is 5 mm.

In particular, FIG. 13 depicts a single passive shield 210 positioned behind the vertex position 30 of the head model. The QBC 100 is placed directly over the vertex position 30. In FIG. 14, the QBC is also in the vertex position 30, and a second passive shield 210 is placed in front of the vertex position 30. In FIGS. 13 and 14, the rear passive shield 210 is located from 20 mm to 30 mm behind the vertex position 30 as denoted by the double arrow line II. In a particular embodiment, the rear passive shield 210 is located 27.5 mm behind the vertex position 30. The front passive shield 210 of FIG. 14 is located from 50 mm to 60 mm in front of the vertex position 30 as denoted by the double arrow line I. In a particular embodiment, the front passive shield 210 is located 52 mm in front of the vertex position 30.

Figure 15:
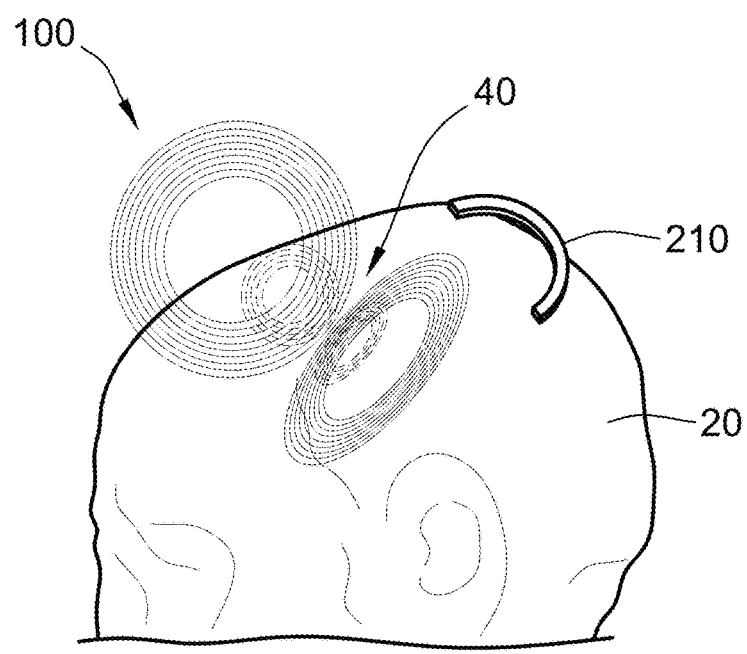
FIG. 15 depicts a QBC with single shield in the dorsolateral prefrontal cortex position over a head model, according to an exemplary embodiment.
Figure 16:
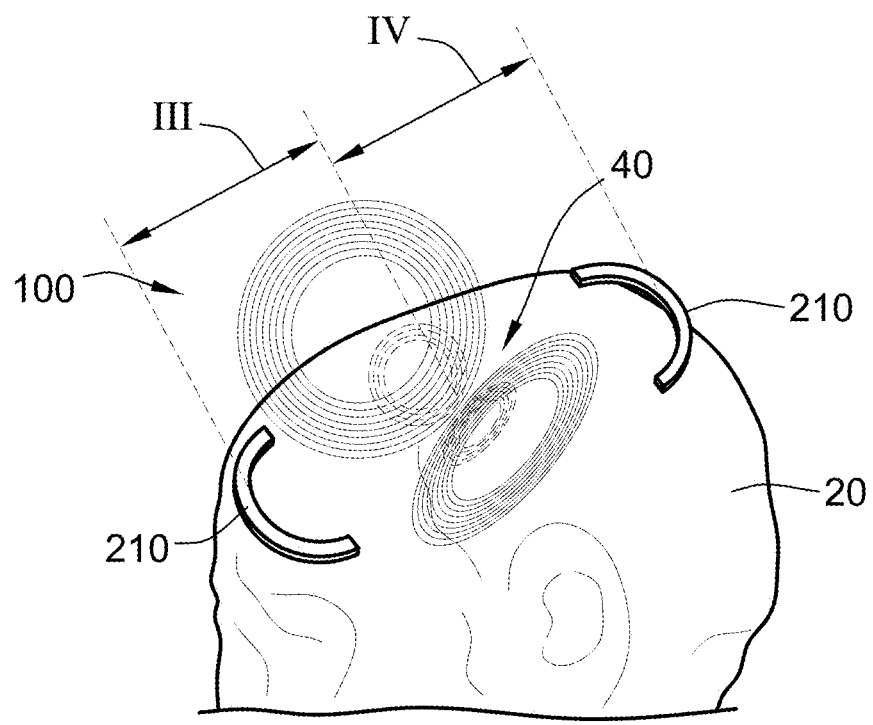
FIG. 16 depicts a QBC with double shield in the dorsolateral prefrontal cortex position over a head model, according to an exemplary embodiment.

In FIGS. 15 and 16, the QBC 100 is located over the dorsolateral prefrontal cortex position 40 of the head model 20. In FIGS. 15 and 16, a passive shield 210 is located behind the QBC 100, and in FIG. 16, a second passive shield 210 is located in front of the QBC 100. The rear passive shields 210 of FIGS. 15 and 16 are located from 80 mm to 90 mm behind the QBC 100 in the dorsolateral prefrontal cortex position 40 as denoted by the double arrow line IV, and the front passive shield 210 of FIG. 16 is located from 70 mm to 90 mm in front of the QBC 100 as denoted by the double arrow line III. In a particular embodiment, the rear passive shield is located 85 mm behind the QBC 100 in the dorsolateral prefrontal cortex position 40, and the front passive shield 210 is located 80 mm in front of the QBC 100. The locations of the passive shields 210 are exemplary only, and in embodiments, the passive shield 210 is moved to various other locations and distances from the QBC 100 based on the particular shape of the passive shield 210, the region of stimulation, and the level of shielding desired.

Based on the position of the passive shields 210 and QBCs 100 in FIGS. 13-16, simulations on the 50 head models were performed using the Sim4Life tool described above. In particular, the passive shield 210 was rotated along the Y-axis by an average of thirty degrees to position it along the scalp for each individual head model. The relative permeability was set at 50,000 for shielding a high magnetic field generated by the QBC 100. The passive shields 210 were positioned in such a way so that they were far enough from the center of the QBC 100 to have small effects on the maximum stimulation intensity, while still being close enough to affect coil focality.

As in the unshielded embodiment described above, the same parameters of interest were investigated, including E-Max brain (the maximum E-Field intensity in the brain—Grey matter & White matter), A-Half (surface area of the brain exposed to E-Field intensities at least one half E-Max), V-Half (the volume of the brain exposed to E-Field intensities at least one half E-Max), and E-Max head (the maximum E-Field intensity in the entire head).

In contrast to other shielding techniques, the passive shield 210 discussed herein utilizes a ferromagnetic material and a semi-circle shape. The semi-circle shape of the passive shield 210 helps to reduce the magnetic field in the surrounding region without affecting the primary region of interest. Furthermore, the curved shape of the passive shield 210 directed the magnetic field vectors toward the region of interest. As can be determined from a comparison of Table 1, above, and Table 2, below, simulation results show no significant difference in the mean value of E-Max when compared to the QBC 100 alone, but the focality is improved.

TABLE 2

Parameters of Interest for QBC with One Shield and QBC with Two Shields

| Coil and position | Parameters of Interest | Values (Mean) |
| --- | --- | --- |
| QBC with single shield at Vertex | V-Half (m$^3$) | 2.36E−06 |
| | E-Max (GM & WM) (V/m) | 138 |
| | E-Max (Entire head) (V/m) | 257 |
| | A-Half (m$^2$) | 10 |
| QBC with double shields at Vertex | V-Half (m$^3$) | 2.31E−06 |
| | E-Max (GM & WM) (V/m) | 136 |
| | E-Max (Entire head) (V/m) | 256 |
| | A-Half (m$^2$) | 10 |
| QBC with single shield at Prefrontal Cortex | V-Half (m$^3$) | 4.07E−06 |
| | E-Max (GM & WM) (V/m) | 162 |
| | E-Max (Entire head) (V/m) | 237 |
| | A-Half (m$^2$) | 16 |
| QBC with double shields at Prefrontal Cortex | V-Half (m$^3$) | 4.07E−06 |
| | E-Max (GM & WM) (V/m) | 161 |
| | E-Max (Entire head) (V/m) | 237 |
| | A-Half (m$^2$) | 16 |

Table 2 explores the effects of both one and two shields 210 with the QBC 100 for both stimulation locations (vertex position 30 and dorsolateral prefrontal cortex 40) and all 50 head models. Simulation results outline a decrease in the V-Half of the QBC 100 with single passive shield 210 (at the vertex position 30) by 11.7% and by 13.4% with double passive shield 210 from QBC 100 alone (see Table 1, above). Also, a 21.4% (single shield) and 22.9% (double shield) decrease is observed in the V-Half when compared to a commercial Figure-8 coil 10 (see Table 1, above), making a significant improvement in the focality. Furthermore, a decrease of 14.4% in V-Half (at the dorsolateral prefrontal cortex position 40) results from the QBC 100 with both single and double passive shield 210, when compared to the QBC 100 alone followed by 25.3% (single and double shield 210) decrease in V-Half when compared with the Figure-8 coil 10 (see Table 1, above). Further details of the V-Half for the single and double passive shield 210 are provided by Table 3, below.

TABLE 3

Five Number Summary of V-Half for QBC with Single and Double Shields

| V-Half (m$^3$) | Vertex | Dorsolateral prefrontal cortex |
| --- | --- | --- |
| QBC with single shield | | |
| Minimum | 1.3290E−07 | 2.9271E−07 |
| First Quartile | 1.0638E−06 | 2.9699E−06 |
| Median | 1.9205E−06 | 3.8905E−06 |
| Third Quartile | 3.4065E−06 | 5.9752E−06 |
| Maximum | 8.4110E−06 | 7.3140E−06 |
| QBC with double shield | | |
| Minimum | 1.3194E−07 | 2.9638E−07 |
| First Quartile | 1.0987E−06 | 2.9693E−06 |
| Median | 1.9024E−06 | 3.9237E−06 |
| Third Quartile | 3.2419E−06 | 5.9724E−06 |
| Maximum | 7.9240E−06 | 7.3120E−06 |

An advantage of the QBC 100 is the angular shape which helps in positioning the passive shield 210 or passive shields 210 below the coils of the QBC 100 without increasing the distance between the coil and scalp. This is not possible with the Figure-8 coil configuration because the windings of the Figure-8 coil are all in one plane, and placing the shield between the head and coil will increase the gap between them. The E-Max gets reduced with increase in the distance between the head and coil due to the decaying property of the magnetic field.

The ratio of electric field on scalp to brain at the dorsolateral prefrontal cortex is 1.80 for the QBC alone, 1.46 for a single passive shield, 1.47 for a double passive shield and 1.47 for the Figure-8 coil. This ratio is an important parameter for determining the stimulation of nerves on the scalp. This change in ratio is representative of a decrease in stimulation intensities at the scalp, while the maximum intensities observed in the brain are not affected. This reduction is around 40 V/m from QBC alone to QBC with the single or double passive shields.

Figure 17:
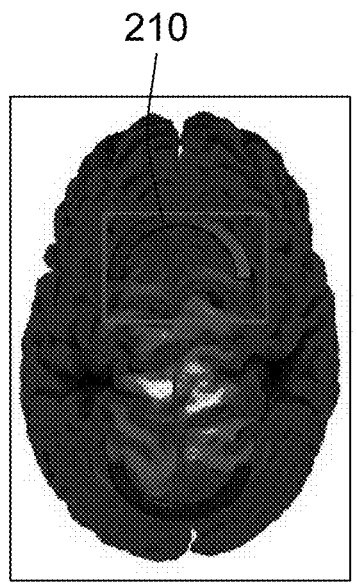
FIG. 17 depicts the induced electric field on the brain of a head model with the QBC and double shield located at the vertex position, according to an exemplary embodiment.
Figure 18:
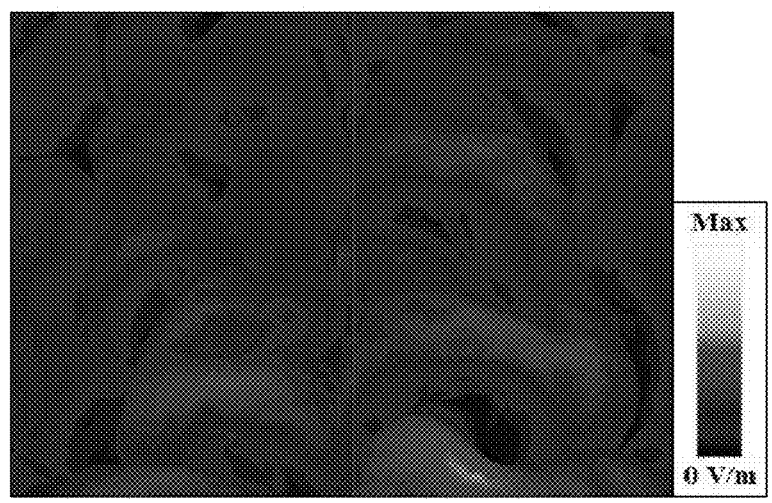
FIG. 18 depicts a magnified view of the induced electric field in the region of a passive shield as shown in FIG. 17.
Figure 19:
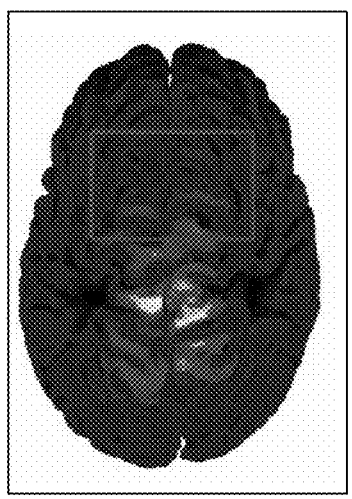
FIG. 19 depicts the induced electric field on the brain of a head model with the QBC alone located at the vertex position, according to an exemplary embodiment.
Figure 20:
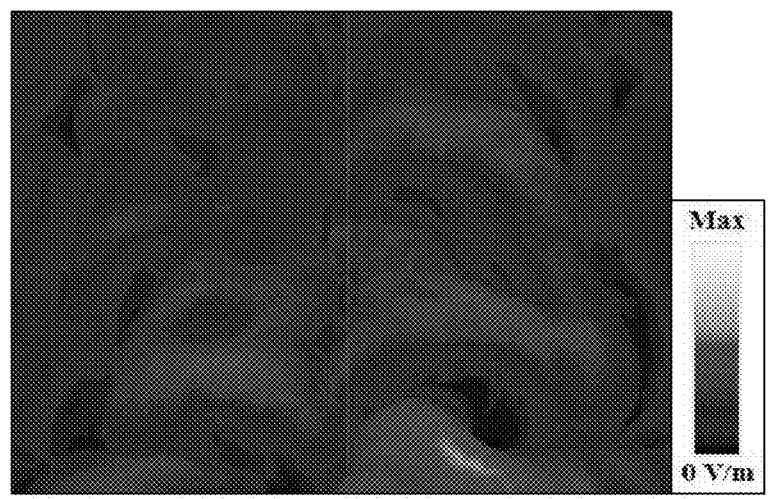
FIG. 20 depicts a magnified view of the induced electric field as shown in FIG. 19.

FIGS. 17-20 illustrate the decrease in the induced electric field in the grey matter of a head model with the use of shields with the QBC. In particular, FIG. 17 depicts the electric field in the grey matter of a head model when a passive shield 210 is utilized. FIG. 18 provides a magnified view of the region near the shield. FIG. 19 depicts the electric field in the grey matter of a head model in the absence of a shield, and FIG. 20 depicts the magnified view of a comparable region as shown in FIG. 18. As can be seen in a comparison of FIGS. 18 and 20, the magnified area of the grey matter near the passive shield shows the decrease in the area of stimulation near the regions where shield has been placed.

Figure 21:
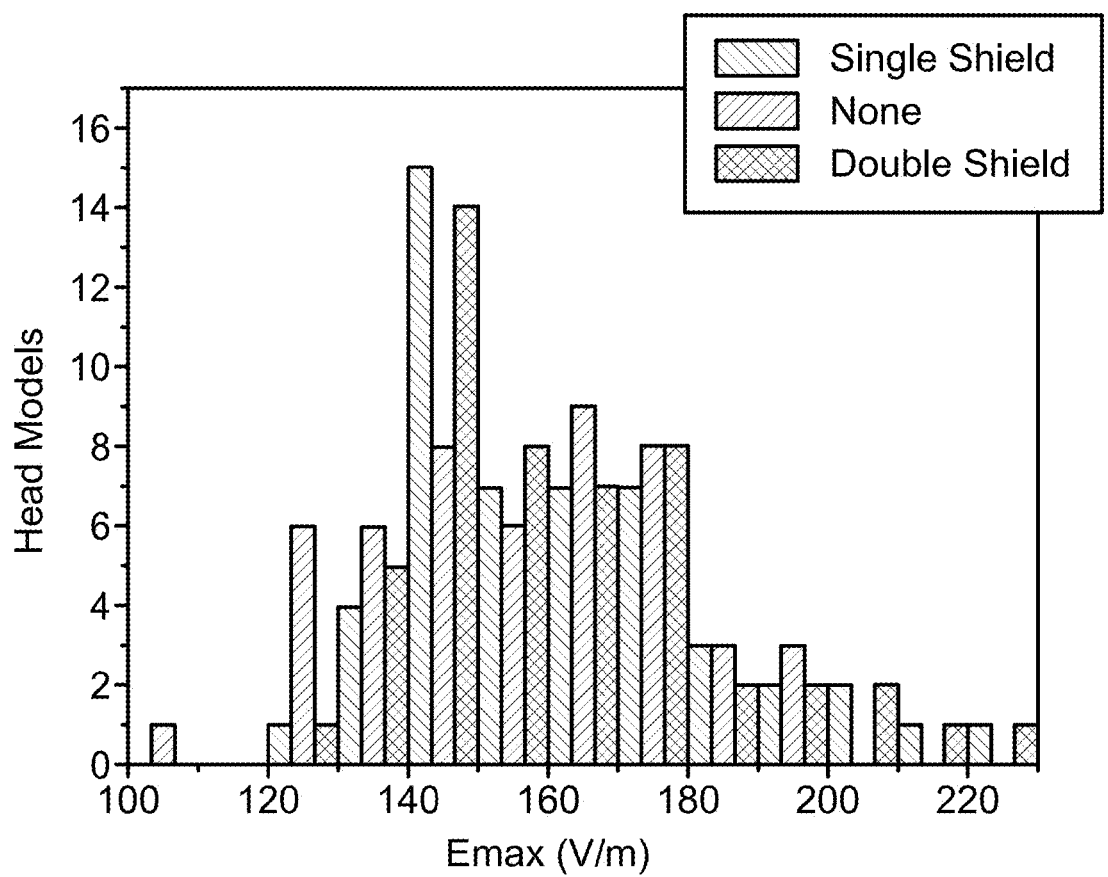
FIG. 21 is a histogram of the maximum electric field in the brain resulting from the QBC alone, the QBC with single shield, and the QBC with double shield located at dorsolateral prefrontal cortex position of fifty head models.
Figure 22:
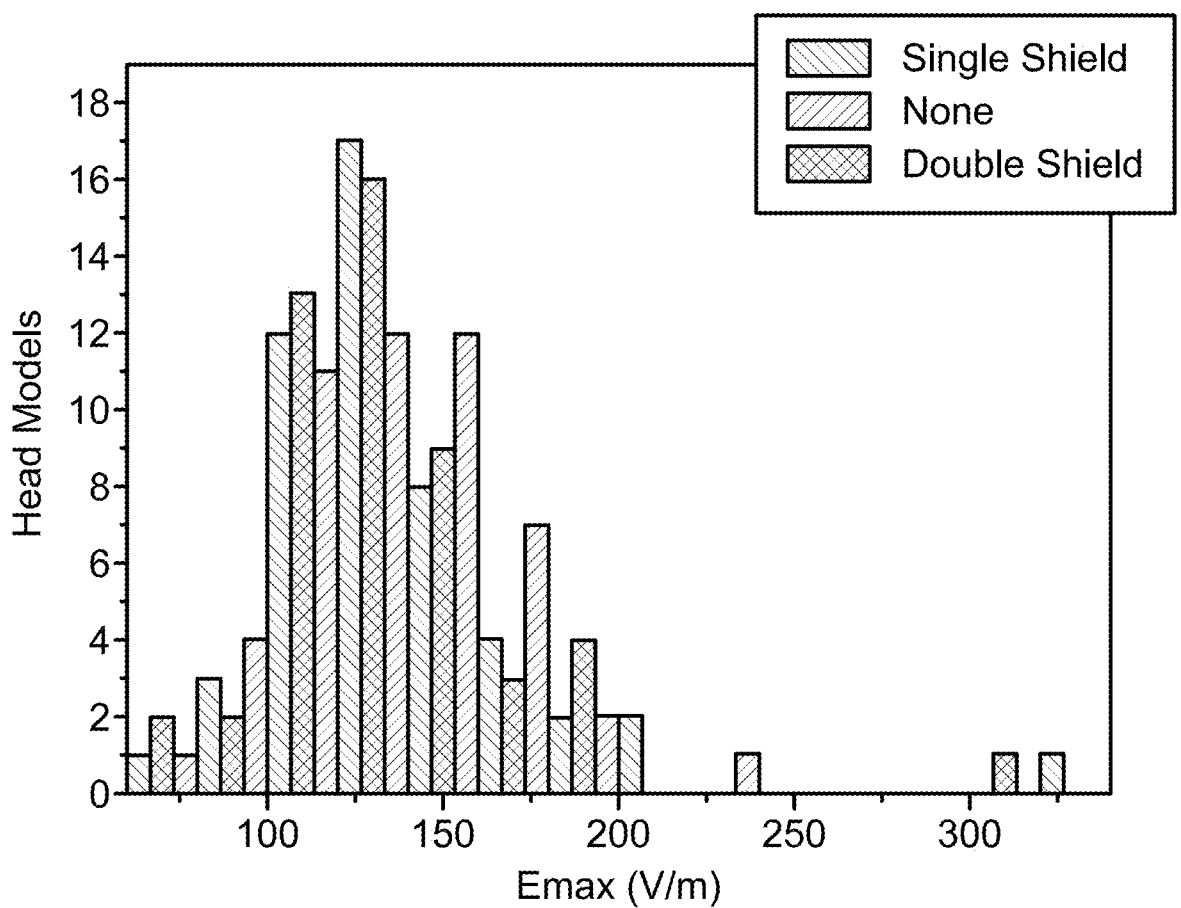
FIG. 22 is a histogram of the maximum electric field in the brain resulting from the QBC alone, the QBC with single shield, and the QBC with double shield located at vertex position of fifty head models.

Histograms of the E-Max in the brain are shown in FIG. 21 for the dorsolateral prefrontal cortex and in FIG. 22 for the vertex region. The histograms provide the distribution of E-Max measurements for all 50 models exposed to the QBC alone, to the QBC with single shield, and to the QBC with the double shield. As can be seen in FIGS. 21 and 22, both the histogram plots are slightly skewed to the right, and an outlier appears in FIG. 22 because the particular head model had less brain to scalp distance, thereby producing a high field in the grey matter. A large, high electric field intensity in an unexpected, isolated region of the brain can be seen in the histograms, which is likely the result of a numerical artifact.

As discussed above, no difference in the E-Max of the QBC with the single passive shield and of the QBC with the double passive shield was observed, but models close to the mean value have greater values of E-Max for QBC with either the single passive shield or the double passive shield in comparison to the QBC alone. Although, as can be seen in FIGS. 20 and 21, this trend does not hold true as the value moves away from the mean.

Figure 23:
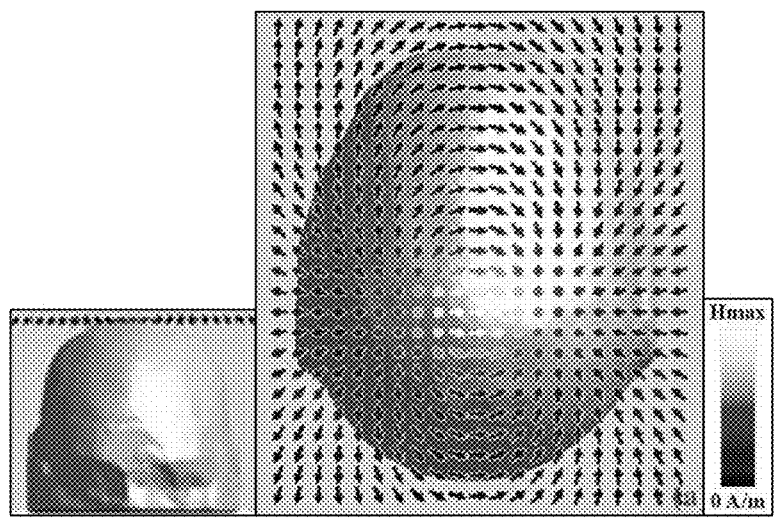
FIG. 23 depicts the magnetic vector field produced by the QBC located at the vertex position.

Further details about how the magnetic field has been shaped by the addition of a passive, ferromagnetic shield are shown in FIGS. 23-26. FIGS. 23 and 25 depict the magnetic field vectors along the coronal and sagittal planes, respectively, for the QBC positioned at the vertex and the dorsolateral prefrontal cortex, respectively. FIGS. 24 and 26 depict the magnetic field vectors along the coronal and sagittal planes, respectively, for the QBC with the passive shield 210 positioned at the vertex and the dorsolateral prefrontal cortex, respectively. When comparing FIGS. 23 and 24 and FIGS. 25 and 26, it can be seen that, in the presence of the passive shield 210, magnetic field vectors which were going away from the brain were rotated towards the coils/brain. Also, the value of the magnetic field vector is large because of the use of ferromagnetic material for the shielding. For example, in FIG. 25, the field vectors at the right, upper corner are going away from the head in the absence of the shield, but as can be seen in FIG. 26, the field vectors in the same region are rotated by few degrees towards the head model in the presence of a shield.

The double shield provided similar results to the single shield at the dorsolateral prefrontal cortex. One of the reasons that adding the second passive shield provided results similar to the single shield when positioned over the dorsolateral prefrontal cortex pertains to the shape of the head. That is, when the QBC was positioned over the dorsolateral prefrontal cortex, the second shield was away from both the coil and head to keep the shields parallel to each other which was one of the reasons for obtaining similar results as compared to the single shield. Also, when shields are placed close to the coils, they reduce the E-Max at the target location which is not desirable.

As discussed herein, the embodiments of the QBC that includes passive ferromagnetic shielding demonstrate improved focality as compared to the QBC alone and especially with respect to the conventional Figure-8 coil (in particular, the Magstim 70 mm coil). The results were demonstrated at two different locations over 50 heterogeneous head models. Further, the single and double passive shield embodiments of the QBC performed almost equally well in improving the focality by nearly 25% when compared to the conventional Figure-8 coil. Beyond brain stimulation, the improvements made to the relative intensity of scalp stimulation could also be an important factor for delivering TMS with greater patient tolerability.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A stimulation device; comprising:
a first set of electromagnetic coils, including a first coil and a second coil, wherein a first angle between the first coil and the second coil is less than 180°; and
a second set of electromagnetic coils, including a third coil and a fourth coil, wherein a second angle between the third coil and the fourth coil is less than 180° and wherein the third coil is smaller in at least one dimension than the first coil and the fourth coil is smaller in at least one dimension than the second coil;
wherein the second set of electromagnetic coils is disposed between the first set of electromagnetic coils; and
wherein the first angle and the second angle share a common vertex.

2. The stimulation device of claim 1, wherein the first coil and the second coil are the same size and shape and the third coil and the fourth coil are the same size and shape.

3. The stimulation device of claim 1, wherein the third coil is at least 50% smaller in the at least one dimension than the first coil and the fourth coil is at least 50% smaller in the at least one dimension than the second coil.

4. The stimulation device of claim 3, wherein the first coil, the second coil, the third coil, and the fourth coil are all circular and wherein the at least one dimension of the third coil is an outside diameter and the at least one dimension of the fourth coil is an outside diameter.

5. The stimulation device of claim 1, wherein the angle between the first coil and the second coil and the angle between the third coil and the fourth coil are each less than 150°.

6. The stimulation device of claim 5, wherein the angle between the first coil and the second coil and the angle between the third coil and the fourth coil are each 45°.

7. The stimulation device of claim 1, wherein current supplied to the first coil, the second coil, the third coil, and the fourth coil is from 1 A to 10 kA.

8. The stimulation device of claim 7, wherein the current supplied is at a frequency of from 1 kHz to 10 kHz.

9. The stimulation device of claim 1, wherein the stimulation device produces an electric field in a head sufficient for depolarization of cortical neurons.

10. The stimulation device of claim 1, further comprising at least one shield made of a ferromagnetic material.

11. A stimulation device, comprising:
a first set of electromagnetic coils, including a first coil and a second coil, wherein an angle between the first coil and the second coil is less than 180°;
a second set of electromagnetic coils, including a third coil and a fourth coil, wherein an angle between the third coil and the fourth coil is less than 180° and wherein the third coil is smaller in at least one dimension than the first coil and the fourth coil is smaller in at least one dimension than the second coil; and
at least one shield made of a ferromagnetic material;
wherein each of the at least one shield is a semi-circular bar with an inside diameter from 40 mm to 55 mm and an outside diameter from 50 mm to 70 mm.

12. The stimulation device of claim 11, wherein each of the at least one shield has a thickness from 2 mm to 5 mm.

13. A stimulation method, comprising the steps of:
positioning a stimulation device over a head, the stimulation device comprising a first set of electromagnetic coils, including a first coil and a second coil, wherein a first angle between the first coil and the second coil is less than 180°, and a second set of electromagnetic coils, including a third coil and a fourth coil, wherein a second angle between the third coil and the fourth coil is less than 180°, and wherein the third coil and fourth coil are smaller than the first coil and second coil, wherein the second set of electromagnetic coils is disposed between the first set of electromagnetic coils, and wherein the first angle and the second angle share a common vertex;
supplying current to the stimulation device; and
stimulating one or more neural networks of a brain in the head.

14. The stimulation method of claim 13, wherein the step of positioning the stimulation device over the head further comprises positioning the stimulation device over the vertex of the head.

15. The stimulation method of claim 14, further comprising positioning a first ferromagnetic shield a lateral distance of from 20 mm to 30 mm away from the stimulation device and towards the rear of the head.

16. The stimulation method of claim 15, further comprising positioning a second ferromagnetic shield a lateral distance of from 50 mm to 60 mm away from the stimulation device and towards the front of the head.

17. The stimulation method of claim 13, wherein the step of positioning the stimulation device over the head further comprises positioning the stimulation device over the dorsolateral prefrontal cortex of the head.

18. The stimulation method of claim 17, further comprising positioning a first ferromagnetic shield a lateral distance of from 80 mm to 90 mm away from the stimulation device and towards the rear of the head.

19. The stimulation method of claim 18, further comprising positioning a second ferromagnetic shield a lateral distance of from 70 mm to 90 mm away from the stimulation device and towards the front of the head.

20. The stimulation method of claim 13, wherein the step of stimulating one or more neural networks of a brain in the head further comprises producing an electric field in the head sufficient for depolarization of cortical neurons.

\* \* \* \* \*